(12) United States Patent
Mirkin et al.

(10) Patent No.: US 7,361,310 B1
(45) Date of Patent: Apr. 22, 2008

(54) DIRECT WRITE NANOLITHOGRAPHIC DEPOSITION OF NUCLEIC ACIDS FROM NANOSCOPIC TIPS

(75) Inventors: Chad A. Mirkin, Evanston, IL (US); Linette Demers, Evanston, IL (US); David S. Ginger, Evanston, IL (US)

(73) Assignee: Northwestern University, Evanston, IL (US)

( * ) Notice: Subject to any disclaimer, the term of this patent is extended or adjusted under 35 U.S.C. 154(b) by 599 days.

(21) Appl. No.: 10/307,515

(22) Filed: Dec. 2, 2002

Related U.S. Application Data

(60) Provisional application No. 60/362,924, filed on Mar. 7, 2002, provisional application No. 60/337,598, filed on Nov. 30, 2001.

(51) Int. Cl.
*B01L 3/02* (2006.01)

(52) U.S. Cl. .................. 422/100; 422/63; 422/64; 422/65; 422/101; 436/180; 435/6; 73/105

(58) Field of Classification Search ............ 435/6; 422/63–65, 99–101; 204/400; 436/180, 436/6; 73/105
See application file for complete search history.

(56) References Cited

U.S. PATENT DOCUMENTS

| | | | |
|---|---|---|---|
| 4,626,501 A | 12/1986 | Landes | |
| 5,202,004 A * | 4/1993 | Kwak et al. | 205/790.5 |
| 5,363,697 A | 11/1994 | Nakagawa | |
| 5,472,881 A | 12/1995 | Beebe et al. | |
| 5,744,305 A | 4/1998 | Fodor et al. | |
| 5,747,334 A | 5/1998 | Kay et al. | |
| 5,763,768 A | 6/1998 | Henderson et al. | |
| 5,837,832 A | 11/1998 | Chee et al. | |
| 5,874,668 A * | 2/1999 | Xu et al. | 73/105 |
| 5,962,736 A | 10/1999 | Zambias et al. | |
| 5,965,721 A | 10/1999 | Cook et al. | |
| 5,985,353 A | 11/1999 | Lawton et al. | |
| 5,985,356 A | 11/1999 | Schultz et al. | |
| 6,037,124 A | 3/2000 | Matson | |

(Continued)

FOREIGN PATENT DOCUMENTS

WO    WO 96/31625 A1    10/1996

(Continued)

OTHER PUBLICATIONS

Bruchez, Jr., M., et al., "Semiconductor Nanocrystals as Fluorescent Biological Labels", *Science*, vol. 281 p. 2013 (1998).

(Continued)

*Primary Examiner*—Jill Warden
*Assistant Examiner*—Jyoti Nagpaul
(74) *Attorney, Agent, or Firm*—Foley & Lardner LLP

(57) ABSTRACT

The use of direct-write nanolithography to generate anchored, nanoscale patterns of nucleic acid on different substrates is described, including electrically conductive and insulating substrates. Modification of nucleic acid, including oligonucleotides, with reactive groups such as thiol groups provides for patterning with use of appropriate scanning probe microscopic tips under appropriate conditions. The reactive groups provide for chemisorption or covalent bonding to the substrate surface. The resulting nucleic acid features, which exhibit good stability, can be hybridized with complementary nucleic acids and probed accordingly with use of, for example, nanoparticles functionalized with nucleic acids. Patterning can be controlled by selection of tip treatment, relative humidity, and nucleic acid structure.

27 Claims, 16 Drawing Sheets

U.S. PATENT DOCUMENTS

| | | | |
|---|---|---|---|
| 6,270,946 B1 | 8/2001 | Miller | |
| 6,287,765 B1 | 9/2001 | Cubicciott | |
| 6,323,029 B1 | 11/2001 | Butler et al. | |
| 6,361,944 B1 | 3/2002 | Mirkin et al. | |
| 6,379,932 B1 | 4/2002 | Arnold et al. | |
| 6,410,231 B1 | 6/2002 | Arnold et al. | |
| 6,417,340 B1 | 7/2002 | Mirkin et al. | |
| 6,534,267 B1 | 3/2003 | Wang et al. | |
| 6,573,369 B2* | 6/2003 | Henderson et al. | 536/23.1 |
| 6,635,311 B1 | 10/2003 | Mirkin et al. | |
| 6,642,129 B2 | 11/2003 | Liu et al. | |
| 6,674,074 B2 | 1/2004 | Schwartz | |
| 6,716,578 B1 | 4/2004 | Henderson et al. | |
| 6,737,646 B2 | 5/2004 | Schwartz | |
| 2001/0044106 A1* | 11/2001 | Henderson et al. | 435/6 |
| 2002/0025534 A1 | 2/2002 | Goh et al. | |
| 2002/0034756 A1 | 3/2002 | Lestinger et al. | |
| 2002/0063212 A1 | 5/2002 | Mirkin et al. | |
| 2002/0122873 A1 | 9/2002 | Mirkin et al. | |
| 2002/0123135 A1 | 9/2002 | Henderson | |
| 2002/0165675 A1 | 11/2002 | Golovlev | |
| 2002/0172953 A1 | 11/2002 | Mirkin et al. | |
| 2003/0068446 A1 | 4/2003 | Mirkin et al. | |
| 2003/0068638 A1 | 4/2003 | Cork et al. | |
| 2003/0087277 A1 | 5/2003 | Fritzsche et al. | |
| 2003/0092029 A1 | 5/2003 | Josephson et al. | |
| 2004/0026007 A1 | 2/2004 | Hubert | |

FOREIGN PATENT DOCUMENTS

| | | |
|---|---|---|
| WO | WO 98/04740 A1 | 2/1998 |
| WO | WO 99/31267 A1 | 6/1999 |
| WO | WO 00/04382 A1 | 1/2000 |
| WO | WO 00/04389 A1 | 1/2000 |
| WO | WO 00/04390 A1 | 1/2000 |
| WO | WO 00/36136 A1 | 6/2000 |
| WO | WO 00/41213 A1 | 7/2000 |
| WO | WO 00/46406 A2 | 8/2000 |
| WO | WO 02/45215 A2 | 6/2002 |

OTHER PUBLICATIONS

Cui, Y., et al, "Nanowire Nanosensors for Highly Sensitive and Selective Detection of Biological and Chemical Species", Science, vol. 293, p. 1289 (2001).

Demers, L., et al., "A Fluorescence-Based Method for Determining the Surface Coverage and Hybridization Efficiency of Thiol-Capped Oligonucleotides Bound to Gold Thin Films and Nanoparticles", Anal. Chem. vol. 72, pp. 5535-5541 (2000).

Demers, L., et al., "Direct Patterning of Modified Oligonucleotides on Metals and Insulators by Dip-Pen Nanolithography", Science, vol. 296, p. 1836, including supplementary material (2002).

Demers, L., et al., "Orthogonal Assembly of Nanoparticle Building Blocks on Dip-Pen Nanolithographically Generated Templates of DNA", Angnew. Chem. Int. Ed., vol. 40, No. 16, p. 3071 (2001).

Demers, L., "Direct-Patterning of DNA via Dip-Pen Nanolithography", Thesis of Demers, Ch. 6 (Jun. 2002).

Frisbie, C., et al., "Functional Group Imaging by Chemical Force Microscopy", Science, vol. 265, p. 2071 (1994).

Gibson, G., et al., "A Primer of Genome Science", Chapter 3 (2002).

Gibson, G., et al., "A Primer of Genome Science", Chapter 4 (2002).

Henke, C., "DNA-chip technologies", IVD Technology Magazine (Sep. 1998).

Herne, T. M., et al., "Characterization of DNA Probes Immobilized on Gold Surfaces", J. Am. Chem. Soc. vol. 119, No. 38, pp. 8916-8920 (1997).

Hong, S., et al., "A Nanoplotter with Both Parallel and Serial Writing Capabilities", Science, vol. 288, p. 1808 (2000).

Hong, S., et al., "Multiple Ink Nanolithography: Toward a Multiple-Pen Na no-Plotter", Science, vol. 286, p. 523 (1999).

Ivanisevic, A., et al., "'Dip-Pen' Nanolithography on Semiconductor Surfaces", J. Am. Chem. Soc. vol. 123, pp. 7887-7889 (2001).

Jang, J., et al., "Self-assembly of ink molecules in dip-pen nanolithography: A diffusion model", J. Chem. Phys., vol. 115, No. 6, p. 2721 (2001).

Kenny, M., et al., "Mutation Typing Using Electrophoresis and Gel-Immobilized Acrydite™ Probes", BioTechniques, vol. 25, No. 3, p. 516 (1998).

Kurth, D., et al., "Surface Reactions on Thin Layers of Silane Coupling Agents", Langmuir, vol. 9, No. 11, pp. 2965-2973 (1993).

Lee, K., et al., "Protein Nanoarrays Generated By Dip-Pen Nanolithography", Science, vol. 295, p. 1702 (2002).

Letsinger, R., et al., "Use of a Steroid Cyclic Disulfide Anchor in Constructing Gold Nanoparticle-Oligonucleotide Conjugates", Bioconjugate Chem., vol. 11, No. 2, pp. 289-291 (2000).

Levicky, R., et al., "Using Self-Assembly To Control the Structure of DNA Monolayers on Gold: A Neutron Reflectivity Study", J. Am. Chem. Soc., vol. 120, pp. 9787-9792 (1998).

Maynor, B.W., et al., "Au 'Ink' for AFM 'Dip-Pen' Nanolithography", Langmuir, vol. 17, pp. 2575-2578 (2001).

Mirkin, C.A., "Programming the Assembly of Two- and Three-Dimensional Architectures with DNA and Nanoscale Inorganic Building Blocks", Inorg. Chem. vol. 39, pp. 2258-2272 (2000).

Nicewarner-Peña, S. R., et al., "Submicrometer Metallic Barcodes", Science, vol. 294, p. 137 (2001).

Niemeyer, C. M., Nanoparticles, Proteins, and Nucleic Acids: Biotechnology Meets Materials Science, Angew. Chem. Int. Ed. vol. 40, pp. 4128-4158 (2001).

Noy, A., et al., "Fabrication of Luminescent Nanostructures and Polymer Nanowires Using Dip-Pen Nanolithography", Nano Lett., vol. 2, No. 2, p. 109 (2002).

Noy, A., et al, "Chemical Force Microscopy: Exploiting Chemically-Modified Tips To Quantify Adhesion, Friction, and Functional Group Distributions in Molecular Assemblies", J. Am. Chem. Soc. vol. 117, pp.7943-7951 (1995).

Noy, A., et al., "Chemically-Sensitive Imaging in Tapping Mode by Chemical Force Microscopy: Relationship between Phase Lag and Adhesion", Langmuir, vol. 14, pp. 1508-1511 (1998).

Piner, R. D., et al., "'Dip-Pen' Nanolithography", Science, vol. 283, p. 661 (1999).

Piner, R. D., et al., "Improved Imaging of Soft Materials with Modified AFM Tips", Langmuir, vol. 15, pp. 5457-5460 (1999).

Schwartz, P. V., "Meniscus Force Nanografting: Nanoscopic Patterning of DNA", Langmuir, vol. 17, pp. 5971-5977 (2001).

Schwartz, P. V., "Molecular Transport from an Atomic Force Microscope Tip: A Comparative Study of Dip-Pen Nanolithography", Langmuir, vol. 18, pp. 4041-4046 (2002).

Storhoff, J. J., et al., "Programmed Materials Synthesis with DNA", Chem. Rev. vol. 99, pp. 1849-1862 (1999).

Storhoff, J. J., et al., "One-Pot Colorimetric Differentiation of Polynucleotides with Single Base Imperfections Using Gold Nanoparticle Probes", J. Am. Chem. Soc., vol. 120, pp. 1959-1964 (1998).

Weinberger, D. A., et al., "Combinatorial Generation and Analysis of Nanometer- and Micrometer-Scale Silicon Features via 'Dip-Pen' Nanolithography and Wet Chemical Etching", Adv. Mater. vol. 12, No. 21, p. 1600 (2000).

Wilbur, J. L., et al., "Scanning Force Microscopies Can Image Patterned Self-Assembled Monolayers", Langmuir, vol. 11, pp. 825-831 (1995).

Wilson, D. L., et al., "Surface organization and nanopatterning of collagen by dip-pen nanolithography", PNAS, vol. 98, No. 24, pp. 13660-13664 (2001).

PCT/US02/38252, International Search Report, (2 pgs.) (May 28, 2003).

Amro, N. A., et al., "Patterning Surfaces Using Tip-Directed Displacement and Self-Assembly", Langmuir, vol. 16, No. 7, pp. 3006-3009 (2000).

European Search Report, counterpart for EP No. 02 79 5703, (Feb. 4, 2005).

* cited by examiner

DIRECT WRITE NANOLITHOGRAPHIC DEPOSITION OF NUCLEIC ACIDS FROM NANOSCOPIC TIPS

This application claims benefit of provisional application Ser. No. 60/337,598 filed Nov. 30, 2001, ("Patterning of Nucleic Acids by Dip-Pen Nanolithography" to Mirkin et al.) and to provisional application Ser. No. 60/362,924 filed Mar. 7, 2002, ("Direct Patterning of Oligonucleotides on Metal and Insulator Surfaces via Dip-Pen Nanolithography"), the complete disclosures of which are hereby incorporated by reference.

This invention was made with government support under Grant Nos: EEC011802 from the National Science Foundation F49620-00-1-0283 from the Air Force Office Of Scientific Research, HG02463 from the National Institute of Health, and DAAG55-97-01-0133 from the Army Research Office. The government has rights in the invention.

BACKGROUND

Nanotechnology has many applications throughout biology, biochemistry, chemistry, medicine, genetics, diagnostics, and therapeutics. In addition to generating totally new technologies, nanotechnology also promises to further enable existing technologies to be miniaturized to sub-micron levels. Too often, technology is limited to the micron scale. For example, nucleic acid microarrays have been commercialized at a micron level for biological and genetics applications including documenting gene expression on a genome-wide scale (see, for example, *A Primer of Genome Science*, G. Gibson and S. Muse, 2002, Chapters 3-4). Present microarrays include the cDNA and oligonucleotide types. A strong commercial need now exists, however, to make arrays on a much smaller, nanometer scale, particularly at lateral dimensions of less than about 100 nm. In other words, nucleic acid nanoarrays are needed with much higher densities of sample sites, which approach the size of single molecules, monolayers, and sub-100 nm dimensions. Production methods used to produce microarrays, however, generally are not capable of nanoarray production. Moreover, currently used robotic printing of these arrays can suffer from the printing pins being expensive, fragile, prone to clogging, poor uniformity, and tendency to deliver doughnut-shaped spots as the nucleic acid spreads away from the tip. In addition to nucleic acid arrays, peptide arrays are also important, and at times, combined nucleic acid and peptide structures are of interest. Hence, novel nanotechnology is needed which enables the production of nanoarrays at a commercial level and pushes the limits of microarray miniaturization. In particular, difficulties become more severe when breaking the sub-100 nm barrier, when entering the realm of single molecules and monolayers, and when entering the commercial marketplace.

Nanoscopic tips including scanning probe microscopic (SPM) tips have generally been used to characterize nanoscale structures but their use in fabrication at the nanoscale is much less developed. Early attempts at fabrication were not successful. A need exists to make better use of nanoscopic SPM tips in nanoscale fabrication including, for example, the production of nanoarrays with applications both in the biological and non-biological arts. SPM tips are of particular interest if they can be used for direct writing and patterning of substrates at a molecular level. The challenge of direct writing at this level is particularly significant for direct writing of biological compounds including nucleic acids. Improvements are needed which provide, for example, better resolution, higher reproducibility, better stability, and better retention of molecular recognition and hybridization. One particularly important challenge is the direct writing of single nucleic acid strands, wherein molecular size and charge effects may become important, factors which generally are less relevant for direct writing of uncharged, small molecules. Indirect methods are known for generation of nucleic acid structures at small scales, wherein for example nucleic acids are absorbed to existing lithographic features. Nevertheless, direct writing provides significant advantages over indirect pathways.

One method for direct write nanolithography is DIP PEN NANOLITHOGRAPHY™ printing and deposition (i.e., DPN™ printing and deposition), which is described further below and is being developed at Northwestern University in the Mirkin group and at NanoInk, Inc. (Chicago, Ill.). DPN™ and DIP PEN NANOLITHOGRAPHY™ are trademarks of NanoInk, Inc. This method is versatile and can be carried out with readily accessible equipment. Complicated stamps and resists are not generally needed. Despite the success of this technology to date, improvements are still needed.

Finally, interest in generating nucleic acid features on a nanoscale also arises because of the ability these compounds have to recognize and bind to complementary strands of nucleic acid (i.e., hybridize) which could provide for "bottom-up" nanoscale manufacturing of functional materials including molecular electronic and photonic devices. Programmed materials synthesis with DNA is described in, for example, Mirkin, *Inorganic Chem.*, 2000, 39, 2258-2272; Mirkin, *MRS Bulletin*, January, 2000, pgs. 43-54; and Storhoff et al., *Chem. Rev.*, 1999, 99, 1849-1862. Also, hybridization of nucleic acids is discussed in the context of surface-confined DNA probe arrays in, for example, Herne et al., *J. Am. Chem. Soc.*, 1997, 119, 8916-8920; Levicky et al., *J. Am. Chem. Soc.*, 1998, 120, 9787-9792. Diagnostic applications are also important as discussed in, for example, U.S. Pat. No. 6,361,944 to Mirkin et al. (Nanosphere, Inc.).

SUMMARY

In this section, the inventions disclosed herein are summarized, but this summary does not limit the scope of the invention, which is described in detail and claimed further below.

The present invention, briefly, provides for a method for depositing nucleic acid onto a substrate by direct-write nanolithography comprising the step of positioning at least one nanoscopic tip relative to a substrate so that the tip approaches the substrate, wherein nucleic acid is transferred from the tip to the substrate to generate a stable nucleic acid nanoscale pattern which can be hybridized with complementary nucleic acid.

Briefly, the present invention also provides a method for generating nanoscale patterns of nucleic acid on a substrate comprising positioning a scanning probe microscopic tip relative to the substrate so that the tip approaches the substrate at a relative humidity sufficiently high so that nucleic acid is transferred from the tip to the substrate to form a nanoscale pattern, wherein before transfer the tip is modified to allow the nucleic acid to wet the tip and the nucleic acid is modified to chemisorb or covalently bond to the substrate.

Briefly, the present invention also provides a method for direct patterning of modified nucleic acid onto a substrate comprising the steps of inking a scanning probe microscopic tip with a modified nucleic acid and positioning the inked tip close enough to the substrate to effect transfer of the nucleic acid to the substrate to form a nanoscale pattern, wherein the nucleic acid is modified with a functional group which provides for chemisorption or covalent bonding to the substrate, and the functional group is bonded to the nucleic acid via a spacer.

Still further, the invention also provides a method for direct patterning of modified nucleic acid onto a substrate comprising the step of positioning a scanning probe microscopic tip inked with a modified nucleic acid and positioning the inked tip close enough to the substrate to effect transfer of the nucleic acid to the substrate to form a nanoscale pattern, wherein the nucleic acid is modified with an electrophilic or nucleophilic functional group which provides for covalent bonding to the substrate.

In addition, the invention, briefly, provides a method for improving the transfer of nucleic acid from a scanning probe microscopic tip to a substrate during direct write nanolithography comprising modifying the tip to make it positively charged.

Briefly, the invention also provides a method for improving direct write deposition of nucleic acid from a scanning probe microscope tip to a substrate comprising the step of treating the tip with one or more compositions which improves adhesion of the nucleic acid to the tip.

The invention also provides, briefly, a method for assembling nanoparticles to form nanoscale patterns comprising the steps of: (a) depositing from a nanoscopic tip a first nucleic acid onto a substrate to form a deposit with lateral nanoscale features of about 1,000 nm or less by direct write nanolithography; (b) hybridizing the nucleic acid deposit with the nanoparticle, wherein the nanoparticle is functionalized with a second nucleic acid which is either (1) complementary to the first, or (2) complementary to the nucleic acid of a linking strand which links the second nucleic acid to the first.

Further, the invention also provides a method for assembling nanoparticles to form nanoscale patterns comprising the step of hybridizing a nucleic acid nanoscale deposit on a substrate, the deposit comprising a first nucleic acid, with a nanoparticle, wherein the nanoparticle is functionalized with a second nucleic acid which is either (1) complementary to the first, or (2) complementary to the nucleic acid of a linking strand which links the second nucleic acid to the first.

Still further, the invention provides a nanoscale nucleic acid pattern on a substrate comprising the substrate and at least one pattern of a first nucleic acid on the substrate, wherein the pattern of first nucleic acid is chemisorbed or covalently bonded to the substrate, has a lateral dimension of 1,000 nm or less, and is hybridizable to a second nucleic acid complementary to the first.

The invention provides a nucleic acid nanoarray comprising a substrate and a plurality of patterns of nucleic acid on the substrate, wherein the patterns of nucleic acid are chemisorbed or covalently bonded to the substrate, have lateral dimensions of about 1,000 nm or less and are separated from each other by distances of 1,000 nm or less, have a pattern density of at least 100,000 per square centimeter, and are hybridizable to complementary nucleic acids.

In addition, the invention also includes articles comprising substrates with nucleic acid patterns thereon, nucleic acid nanoarrays, scanning probe microscopic (SPM) tips coated with nucleic acid, solutions used to coat SPM tips, kits for direct write nanolithography of nucleic acids, and computer software for same.

Basic and novel features of the invention, which are discussed in detail below, are many and include the advantages of DPN printing already established in the art including the ability to directly write preconceived nanoscale features without use of expensive and potentially destructive methods such as electron beam and photolithographic methods. Also, the structures can be built up, if desired, without degrading existing structures. Complicated stamps and resists are not needed. Improvements in the consistency and stability of the nanolithography can be observed.

DETAILED DESCRIPTION

Figure 1:
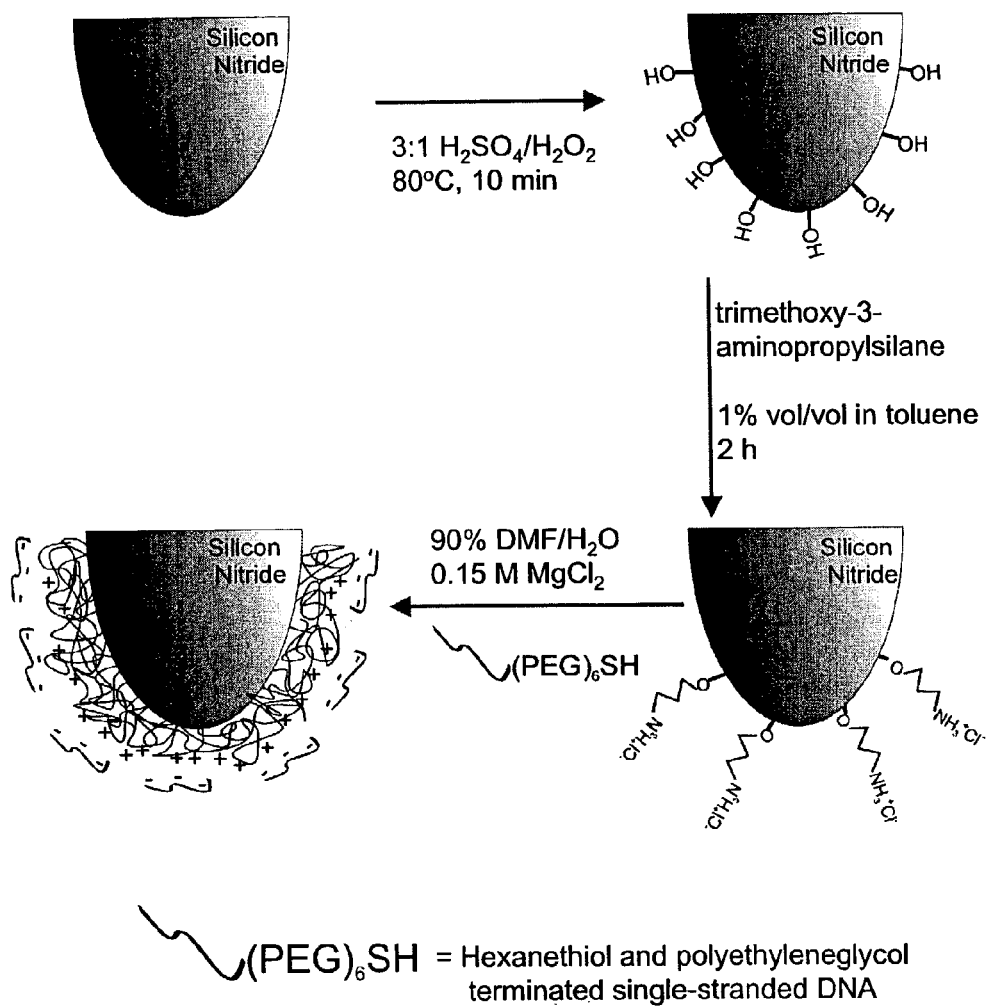
FIG. 1 illustrates coating a silicon nitride tip with a hexanethiol and polyethylene glycol terminated single stranded DNA.

DPN printing, patterning, and deposition methods are disclosed in, for example, the following references from the Mirkin group, which are hereby incorporated by reference in their entirety: (1) Piner et al., *Science,* 283, Jan. 29, 1999, page 661; (2) Hong et al., *Science,* 286, Oct. 15, 1999, page 523; and (3) Hong et al., *Science,* 288, Jun. 9, 2000, page 1808. Further, the technical publication "Direct Patterning of Modified Oligonucleotides on Metals and Insulators by Dip-Pen Nanolithography", by Demers et al., *Science, Vol.* 296, Jun. 7, 2002, pgs. 1836-1838, is also hereby incorporated by reference in its entirety, including the supporting online material cited therein. DPN printing and patterning of nucleic acids, as well as nanoparticulate nucleic acid probes, have been noted in the following references, which are hereby incorporated by reference: (1) C. A. Mirkin, *Mater. Res. Soc. Bull.,* 25, 43 (2000), (2) C. A. Mirkin, *Inorg. Chem.,* 39, 2258 (2000).

Also, provisional patent application Ser. No. 60/337,598 to Mirkin et al, filed Nov. 30, 2001 entitled "Patterning of Nucleic Acid by Dip Pen Nanolithography" is hereby incorporated by reference in its entirety.

Also incorporated by reference in its entirety is the Ph.D. thesis by L. M. Demers, Northwestern University, June 2002, "Nanolithography and Biomolecular Recognition as Tools for the Directed Assembly and Study of Particle-Based Materials," Chapter 6, "Direct-Patterning of DNA via Dip-Pen Nanolithography."

Materials, devices, instruments, software and hardware, articles, and consultation related to DPN printing are also available from Nanolnk, Inc. (Chicago, Ill.).

Additional technical publications relating to SPM probes and nucleic acid deposition and which are hereby incorporated by reference include: (1) "Meniscus Force Nanografting: Nanoscopic Patterning of DNA," Schwartz, *Langmuir,* 2001, 17, 5971-5977; (2) "Molecular Transport from an Atomic Force Microscope Tip: A Comparative Study of Dip-Pen Nanolithography," Schwartz, *Langmuir,* 2002, 18, 4041-4046; and (3) WO 02/45215 A2 with international PCT publication date of Jun. 6, 2002 to Mirkin, Schwartz, et al. "Nanolithography Methods and Products Therefor and Produced Thereby." The latter PCT publication, for example, discloses use of patterning solutions comprising nucleic acid and salt, including cationic surfactants and ammonium compounds such as, for example, tridodecylmethylamine. The solutions can be aqueous and can be used to coat the SPM tip.

The role of biomolecules in materials applications is disclosed in the following references, which are hereby incorporated by reference: (1) J. J. Storhoff, C. A. Mirkin, *Chem. Rev.,* 99, 1849 (1999); (2) C. M. Niemeyer, *Angew. Chem. Int. Ed.* 40, 4128 (2001).

In U.S. patent application Ser. No. 09/866,533, filed May 24, 2001 (see also corresponding U.S. patent publication US 2002/0063212 A1 to Mirkin et al. published May 30, 2002), DIP PEN™ nanolithographic printing background and procedures are described in detail covering a wide variety of embodiments including, for example:

background (pages 1-3);
  summary (pages 3-4);
  brief description of drawings (pages 4-10);
  use of nanoscopic scanning probe microscope tips (pages 10-12);
  substrates (pages 12-13);
  patterning compounds including oligonucleotide, DNA, and RNA (pgs. 13-17);
  practicing methods including, for example, coating tips (pages 18-20);
  instrumentation including nanoplotters (pages 20-24);
  multiple layers and related printing and lithographic methods (pages 24-26);
  resolution (pages 26-27);
  arrays and combinatorial arrays (pages 27-30);
  software and calibration (pages 30-35; 68-70);

kits and other articles, tips coated with hydrophobic compounds (pages 35-37);

seven working examples (pages 38-67);

corresponding claims and abstract (pages 71-82); and FIGS. 1-28.

All of the above text, including each of the various subsections enumerated above including the figures, is hereby incorporated by reference in its entirety and form part of the present disclosure, supporting the claims.

In addition, U.S. Patent Publication 20020122873 A1 (application Ser. No. 10/059,593 filed Jan. 28, 2002) to Mirkin et al (published Sep. 5, 2002) is also incorporated by reference in its entirety. It discloses, for example, use of driving forces to control the movement of a deposition or patterning compound from a nanoscopic scanning probe microscopic tip to a substrate. It also discloses a tip having an internal cavity and an aperture restricting movement of a deposition or patterning compound from the tip to the substrate. The rate and extent of movement of the deposition or patterning compound through the aperture can be controlled by the driving force. Nucleic acid can be deposited or patterned by this method using, for example, a positively charged substrate which attracts the negatively charged nucleic acid. Aperture Pen Nanolithographic methods and fountain pen nanolithographic methods can be used to deposit or pattern nucleic acid as described herein.

DIP PEN nanolithographic printing, and the aforementioned procedures, instrumentation, and working examples, can be adapted also to generate improved nucleic acid and DNA articles and nanoarrays as described further herein. As described further herein, the nucleic acid can be varied widely, but oligonucleotides are of particular interest and, in particular, oligonucleotides which have been modified or have chemical structures which provide for covalent bonding or chemisorption to the substrate surface.

To transfer the nucleic acid from the nanoscopic tip to the substrate as a pattern or deposit, the substrate and tip are moved in relation to each other so that they approach each other. The tip can be moved toward the substrate, the substrate can be moved toward the tip, or both the tip and substrate can be moved toward each other.

In general, nanoscopic, submicroscopic tips can be used which are capable of delivering, patterning, or depositing nanoscopic, submicroscopic amounts of nucleic acid patterning compound from the tip to the substrate. Although the nanoscopic tip design is not particularly limited, in general, the nanoscopic tip can have a tapered or substantially tapered end point which is characterized by nanometer, sub-micron level dimensions rather than microscopic dimensions. For example, there can be nanoscopic level tip widths, cavity, or aperture diameters. In general, nanoscopic tips are preferred which are capable of both imaging nanoscopic structures and depositing nanoscopic structures. SPM tips can be used, and a preferred type of SPM tip is the atomic force microscope (AFM) tip. In general, tips can be used which are designed so that they can be coated with ink on their outer surface such as, for example, atomic force microscope tips. Alternatively, tips can be hollow, including tips which have an aperture opening or NSOM tips. The ink can be delivered continuously if desired. An array of tips can be used, as known in the art, wherein each tip can be individually controlled or collectively operated as desired. The tip can be attached to a cantilever or a functional equivalent thereof.

Known SPM and AFM methods can be used including, for example, contact, non-contact, tapping, and lateral force modes.

In studying direct transfer of nucleic acid from an SPM tip to a substrate, several factors can be important which promote nucleic acid patterning into consistent, high quality patterning. These factors are also discussed further in the Working Examples section.

First, for example, the tip can be well-coated with nucleic acid. For example, surface-modification of a conventional silicon nitride AFM cantilever can promote reliable adhesion of the nucleic acid ink to the tip surface. See, for example, FIG. 1. The tip can be modified at the tip surface to have a positive charge including, for example, a positive charge of amino or ammonium groups. Single or multi-step processes can be used to generate tips designed for nucleic acid deposition. For example, a pretreatment step can be carried out which allows the tip to be functionalized in a subsequent step. For example, the tip can be modified to provide a hydroxylated surface and then the hydroxy groups can be further functionalized. The tip can be treated with strong acid and peroxide, including for example sulfuric acid and hydrogen peroxide. After pretreatment, tip functionalization can be accomplished by treating the tips with, for example, a silane coupling agent such as an aminosilane coupling agent, 3'-aminopropyltrimethoxysilane (for example, 1-2 h, 1% v/v solution in toluene).

The silanized tips can then be coated with nucleic acid. Coating can be carried out with use of a solution comprising nucleic acid and salt. The solvent can be an aprotic solvent such as DMF which can be further mixed with water as desired. In general, more aprotic solvent can be used than water so that, for example, about 70% to about 90% by weight of solvent can be aprotic. The salt can be an inorganic salt such as a group II salt or a halide salt including, for example, magnesium chloride. The concentration of the salt can be, for example, about 0.01 M to about 0.4 M, more particularly about 0.1 M to about 0.2 M. The ratio of the salt to the nucleic acid can be varied to provide good deposition conditions and good nanoscopic structures. The concentration of the nucleic acid can be, for example, about 0.1 mM to about 10 mM, and more particularly, about 0.5 mM to about 5 mM.

The tips can be treated by dipping them for less than a minute as desired, for example about 20 s, into the nucleic acid tip coating solution (see Working Examples), and then blowing dry briefly with compressed gas such as, for example, difluoroethane. AFM tips prepared and coated with nucleic acid in this way can be used in direct write printing experiments for several hours, as described herein, before they can be recoated. In addition, tips can be recoated and used again for the same nucleic acid sequence.

Second, control of ambient relative humidity can provide consistent, high quality direct write patterning of nucleic acid. The relative humidity can be controlled to be sufficiently high to provide transfer of the nucleic acid from the tip to the substrate. In general, relative humidities of at least about 25% can be used, and more particularly, about 25% to about 100%, and more particularly, about 40% to about 100%, and more particularly, about 40% to about 50%. For example, ambient patterning can be performed in an environmentally controlled glovebox at a relative humidity of 45±5% at 23±3° C. Relative humidity can be controlled based on other deposition factors which include the nature of the nucleic acid, the nature of the substrate, the nature of the desired pattern (e.g., dot or line), the nature of the nucleic acid solution used to wet the tip, the nature of the tip, and the like. The role of a meniscus can be important with direct write nanolithographic printing using SPM tips, and the size of the meniscus can be related to the relative humidity.

In addition to tip-coating and humidity, selection of the ink-substrate combination can also facilitate the direct writing of nucleic acid into consistent, high quality features. For example, the nucleic acid can be modified to include functional groups which chemisorb or covalently bond to the substrate. A variety of approaches can be used. For example, the functional group for binding the substrate can be directly bonded to the nucleic acid or can be linked to the nucleic acid by a relatively flexible spacer group. Examples of spacer groups include flexible chain oligomers such as alkylene glycols, for example, polyethylene or polypropylene glycol. These can have, for example, 3-20 alkyleneoxy repeat units. The functional group can be, for example, a sulfur-containing moiety such as thiol or disulfide designed to chemisorb to gold surfaces. The procedures can be used to pattern cyclic disulfide-modified nucleic acid and trithiol-modified nucleic acid. The sulfur atom can be bound to hydrocarbon groups such as, for example, alkyl groups, including $C_4$-$C_{18}$ alkyl groups. The functional group can be, for example, an electrophilic group designed to react with a nucleophilic surface, or a nucleophilic group designed to react with electrophilic surfaces. Michael addition reaction, for example, can be used to bond the nucleic acid to the substrate.

For example, hexanethiol, PEG-modified oligonucleotides can be used to directly pattern gold substrates with features ranging from about 50 nm to several micrometers in size. The hexanethiol group of the nucleic acid can provide for chemisorption to the underlying Au surface. Other embodiments which allow the nucleic acid to be modified with functional groups for attaching to the substrate include (1) phosphorothioate groups (see, e.g., U.S. Pat. No. 5,472,881), (2) substituted siloxanes including aminosiloxanes and mercaptoalkylsiloxanes, (3) embodiments described in U.S. Pat. No. 6,361,944, which is hereby incorporated by reference. Types of nucleic acids and their possible modifications are also described further below.

The substrates can be treated so they comprise both nucleic acid and a passivation agent on the substrate. For example, after the substrates are patterned with nucleic acid, they can be passivated. In one passivation embodiment, unpatterned areas of the substrate can be treated with a passivation agent so as to reduce the reactivity of the unpatterned areas of the substrate during further processing. Passivation can be carried out for a number of reasons including, for example, improving the analysis of or detection of the patterned nucleic acid. For example, if hybridization of the nucleic acid is desired by complementary nucleic acid, then the selectivity of the interaction between the nucleic acid patterned areas and the unpatterned areas can be improved through passivation. Passivation can be carried out by immersing the patterned substrates in solutions wherein the solution contains a passivation agent such as an alkane thiol which selectively adsorbs to the unpatterned area of the substrate such as gold. Hence, the passivation agent can comprise one reactive functional group which provides for chemisorption or covalent bonding to the unpatterned substrate, but does not have other functional groups. For example, the passivation agent can comprise a long chain alkyl group which upon adsorption exposes methyl groups to the surface which are generally unreactive to subsequent processing such as nucleic acid hybridization. The passivation can make the rest of the substrate hydrophobic for example. For example, a gold substrate which has already been patterned with a nucleic acid can be immersed in an ethanol solution of 1-octadecanethiol (ODT, 1 mM) for 1 min. This procedure coats the unpatterned gold surface with a hydrophobic monolayer, passivating it towards the non-specific adsorption of DNA or DNA-modified nanoparticles in subsequent hybridization experiments.

In general, the passivation agent can displace the patterned nucleic acid if the nucleic acid is not functionalized to chemisorb to or covalently bond to the substrate. For example, nucleic acid which does not contain a thiol moiety can be displaced from the surface during the ODT treatment.

In another passivation embodiment, the substrate is first patterned with the passivation agent, followed by patterning with nucleic acid. In other words, substrates can be passivated before patterning. For example, substrates can be treated with a passivation agent such as, for example, an adsorption resistant hydrogel to which oligonucleotides and other nucleic acids can be bound. Passivation agents known in the art of microarray technology can be used.

The nucleic acid patterns can be imaged by tapping mode AFM, for example, following the passivation of the substrate by, for example, ODT treatment. This imaging can provide height measurements. In general, the feature height of the nucleic acid pattern as measured by AFM or similar technique can be, for example, about 100 nm or less, or more particularly, about 10 nm or less. For oligonucleotides, height can be, for example, about 2 nm to about 5 nm.

Figure 2:
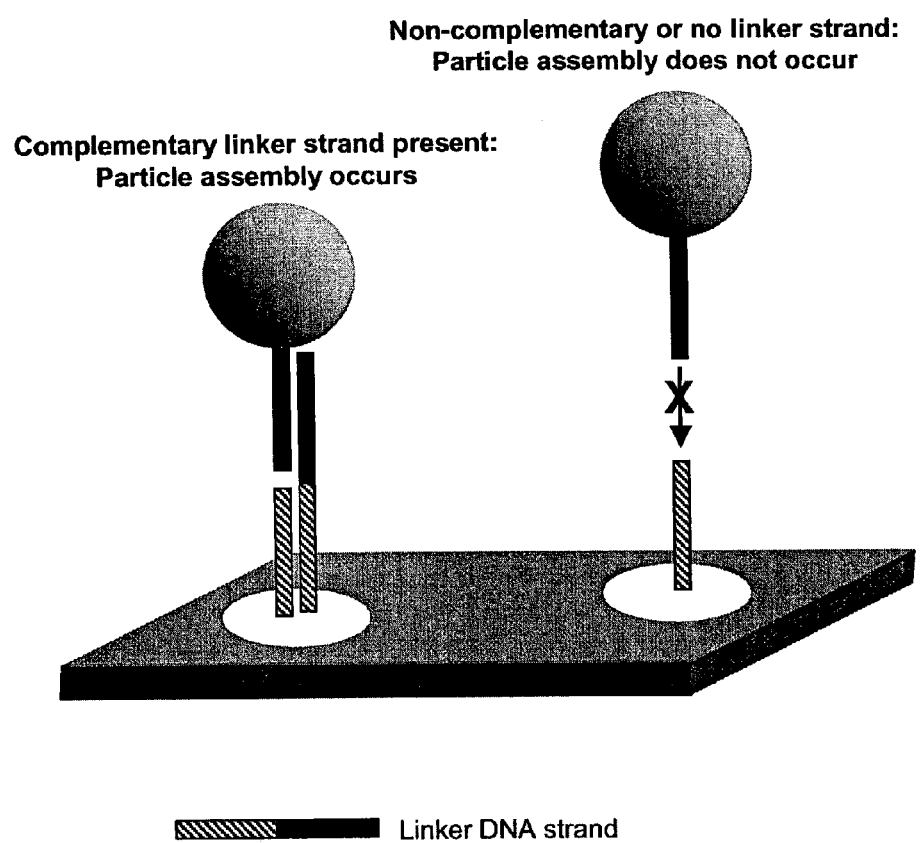
FIG. 2 illustrates use of DNA complementary linker strands to direct particle assembly onto nanoscale features. Particle assembly does not occur with non-complementary linker strand or with no linker strand.

To demonstrate that the patterned, immobilized nucleic acid can retain its highly-specific recognition properties and is accessible to hybridization, nucleic acid patterns can be used to direct the assembly of nanoparticles which comprise complementary nucleic acid (see for example FIG. 2). Structures can be fabricated via this process on the micron to sub-100 nm length scale. The high resolution thus afforded allows control over the placement of individual particles on a surface in the form of a preconceived architecture. Also, the nucleic acid density on the patterns can be sufficiently high to bind nanoparticles in a closely-packed arrangement.

In particle assembly, a three-component system can be applied: (1) patterned nucleic acid, (2) linker nucleic acid, and (3) particle-bound nucleic acid, as described in FIG. 2 and further described in the Working Examples (see also abbreviations therein for C, G, and L types of nucleic acid used below). In this approach, there is a built-in control experiment where the linker can be left out or replaced with a non-complementary sequence. In one such control experiment, for example, 15-mer DNA (G1) modified gold nanoparticles can be hybridized to a 30-mer oligonucleotide, L2, the first 15 bases of which were complementary to the particle-bound DNA. However, the free 15-base segment of the linker can be made not complementary (less than 4 consecutive base overlap) to the DNA on the patterned surface, C1.

The DNA-patterned surfaces can be exposed to non-complementary particle-linker solution under hybridization conditions (e.g., 0.3 M PBS, 0.025% SDS, 3 h, room temperature), but particles bind to the pattern in at most only a few places. Hybridization conditions are known in the art and are described in, for example, U.S. Pat. No. 6,361,944, which is hereby incorporated by reference. A phase AFM image rather than a topography image can be used because better contrast between ODT monolayer, DNA pattern, and gold nanoparticles can be achieved using this imaging mode. Thus, even in the absence of stringency (higher temperature) washes the interactions between the DNA nanopatterns and the oligonucleotide-modified nanoparticles are highly selective, precluding adsorption of particles that are modified with non-complementary DNA. In contrast, a high particle density can be observed on samples where the correct complementary linker oligonucleotide is present.

The stability of patterned nucleic nanostructures on the substrate can be tested by using a patterned surface for particle assembly after it is stored under ambient conditions for more than 3 months. Significantly, a high degree of specific particle adsorption indicates that the pattern can be for the most part intact, with some patchy areas which may be due to degradation of either the nucleic acid, or loss of thiol-modified nucleic acid from the surface. In addition, there can be a small increase in the number of nanoparticles bound to the ODT monolayer regions of the chip (fresh samples exhibit nearly perfectly particle-free backgrounds). A substantial decrease in particle background can be achieved if samples are stored in an inert atmosphere in the dark in order to minimize air and/or photooxidation of the thiol-Au linkages.

An important feature of DPN printing is the ability to generate patterns of specific chemical functionality over a large range of length scales (sub-100 nm to many micron) while exhibiting fine control over feature size. Using the methods described herein, highly-charged macromolecules such as nucleic acid and oligonucleotides can be transferred to a substrate from an SPM tip in much the same way as small hydrophobic molecules.

Specifically, using the methods described herein, the pattern spot size can increase as a function of tip-surface contact time or, alternatively, the line width can be increased by slower draw speeds. For example, the relative humidity can be kept constant at, for example, 45% and nucleic acid spots can be formed by holding a C1 DNA-coated AFM tip at different points on an Au substrate for fixed contact times (minimum of 5 spots at each contact time, ranging from 0.1 s to 100 s). Under these conditions, the transport of DNA from the AFM tip to the surface can follow the same linear increase in pattern area with contact time (spot diameter ~$t^{1/2}$) predicted by theoretical simulations as well as experimentally observed for smaller molecules. Although the rate constants can be different for each ink-substrate pair, this underscores the control DPN printing can offer for patterning compounds ranging from small molecules and salts to organic, charged macromolecules on a variety of substrates.

Also, the rate of nucleic acid pattern formation on gold substrates can be tailored with careful humidity control using the methods described herein. To illustrate and quantify this effect, a series of dots can be formed by holding the tip in contact with a gold substrate for, for example, about 10 s while varying the relative humidity (RH) in the glove box for each spot. Humidity can be increased by, for example, bubbling nitrogen through a container of water and flowing the vapor into the box. The humidity can be kept stable by an automatic controller which alternatively flowed dry nitrogen or water-saturated nitrogen through the box. Before patterns are made, the humidity can be allowed to equilibrate for, for example, at least 5 min at each point after hygrometers placed at the ceiling and floor of the box read the same value (±0.5%). In two separate embodiments (different substrates on a different days, but using the same AFM tip and DNA sequence, (C1) RH can be changed from about 30% to about 46%. Hence, feature size can be varied over a large dynamic range on a reasonable timescale using humidity control. For example, the diameter of a spot created by holding the AFM tip for 10 s can change from less than 50 nm to 1000 nm with a RH increase of 50%. In addition, the affect of relative humidity on the pattern spot size for a given contact time can be well defined. The pattern area can vary roughly as the square of the relative humidity (or spot diameter ~RH) for the humidity range of about 30-80% RH. Note that there can be minimal hysteresis observed upon raising and lowering the humidity. This humidity dependency of DNA patterning generally points to a mechanism for transport of DNA from an AFM tip to a surface that is dependent on a water meniscus between the tip and substrate. In addition, a plot of spot size with respect to humidity can indicate that there is a minimum humidity at room temperature under which the DNA cannot be directly patterned via DPN printing at about 25° C. (for example, x-intercept ~27% RH at 23° C. as shown in the Working Examples, FIGS. 13 and 14). Finally, the fact that a linear regression line can be drawn through points obtained under both high and low humidity conditions for experiments that were performed on different substrates and days underscores the control that humidity provides.

One of the advantageous properties inherent to DPN printing is the capability of generating nanoscale patterns of multiple inks in high registration. To demonstrate multi-nucleic acid ink capabilities, DPN printing can be used to prepare a two-component nucleic acid array. In order to align patterns of two different thiol-modified DNA inks, C1 and C2, without cross-contamination, alignment markers can be first drawn at two different locations on a gold substrate via DPN printing using, for example, a thiol 16-mercaptohexadecanoic acid (MHA). Before patterning, the C1-coated tip can be used to image the MHA markers at low humidity (RH ~25%, DNA does not transport under these conditions) in order to calculate an offset coordinate relative to the MHA patterns. Next, the humidity can be raised to, for example, 45% and a square array of dots (for example, diameter ~760 nm), spaced for example about 2 µm apart can be generated. Likewise, a second pattern, composed of C2 can be positioned in alignment with the first by again imaging an MHA alignment marker with the coated tip at low humidity, calculating an offset coordinate, and then raising humidity and patterning, for example, a triangular array of 100 nm diameter dots. After patterning both nucleic acid inks, the unpatterned areas of the substrate can be passivated by ODT treatment and imaged by tapping mode AFM. To verify the chemical integrity and activity of the patterns, the chip can be exposed to a solution of 13 nm G1-modified gold particles which were hybridized to L1 (complementary to the C1 pattern) under hybridization conditions for 2 h. The substrate can be then rinsed with PBS buffer with 0.025% SDS at 45° C., and then exposed to 30 nm G1-modified particles which are hybridized to L2 (complementary to the C2 pattern). The particles can selectively assemble on the correct patterns with no evidence of cross-contamination on the DNA spots or background. This embodiment not only shows how nanoparticles can be used as diagnostic probes in AFM-based screening procedures, but also nanostructures fabricated via the direct-write DPN printing approach can be used to control the assembly of nanoparticle-based architectures.

Often, DPN printing techniques can be done on gold substrates, which is in some cases undesirable from the standpoint of electronic and optical materials applications. The gold-thiol system provides a useful method for patterning oligonucleotides using DPN printing. However, the electrical conductivity of the gold substrate can prevent the study of charge transport and near-field optical phenomena in nanostructures assembled on such surfaces, and furthermore can quench the emission from any surface-bound fluorophores. To address these issues, and enable electrical and optical characterization of the assembled nanostructures, DPN printing can be used to pattern nucleic acid on electrically insulating surfaces such as, for example, oxidized silicon wafers.

The surface of a thermally oxidized wafer can be activated by treatment with a functional silane coupling agent, such as, for example, 3'-mercaptopropyltrimethoxysilane (MPTMS). The preparation and inking of the AFM tip can be performed as for the patterning of DNA onto gold surfaces, however, oligonucleotides with 5'-terminal acrylamide groups (C3 and C4) can be used in place of oligonucleotides with terminal hexanethiol modifications. Under the DPN printing conditions of room temperature and 45% relative humidity, the acrylamide moieties can react via Michael addition with the pendant thiol groups of the MPTMS to covalently link the nucleic acid to the surface. In addition, nucleic acid pattern formation on silicon oxide substrates shows a similar tip-surface contact time dependence as for gold substrates. Following patterning, the substrate can be passivated by reaction with buffered acrylic acid monomer at pH 10 (e.g., Apogent Discoveries thiol quench buffer). The biological activity of patterned C3 oligonucleotides can be verified by exposing the surface to a solution containing complementary fluorophore-labeled DNA (L3F). The patterns can be subsequently characterized by epi-fluorescence microscopy. DNA nanostructures on silicon generated using this procedure can also be used to direct the assembly of complementary DNA-modified gold nanoparticles (modified with G2). With this technique, DNA spots on silicon oxide surfaces can be generated and detected with diameters of 200 nm, nearly 10,000 times smaller (in terms of areal density), than those in conventional microarrays.

The nucleic acid which is subjected to direct write nanolithography is not particularly limited. For example, the nucleic acid can be synthetically made, modified to include, for example, functional groups tailored for chemisorption or covalent bonding to the substrate, as well as naturally occurring. It can be of low, medium, or high molecular weight, oligomeric or polymeric. It can be single-, double-, or even triple-stranded. The nucleic acid can be based on deoxyribonucleic acid (DNA), ribonucleic acid (RNA), or combinations thereof. The structure of nucleic acids is generally described in, for example, Calladine and Drew, *Understanding DNA, The Molecule and How it Works*, $2^{nd}$ Ed., 1997.

General types of nucleic acid which can be patterned by DPN printing include, for example, DNA, RNA, PNA, CNA, RNA, HNA, p-RNA, oligonucleotides, oligonucleotides of DNA, oligonucleotides of RNA, primers, A-DNA, B-DNA, Z-DNA, polynucleotides of DNA, polynucleotides of RNA, T-junctions of nucleic acids, domains of non-nucleic acid polymer-nucleic acid block copolymers and combinations thereof. Additional general types of nucleic acids include, for example, viral RNA or DNA, a gene associated with a disease, bacterial DNA, fungal DNA, nucleic acid from a biological source, nucleic acid which is a product of a polymerase chain reaction amplification, nucleic acid contacted with nanoparticles, and nucleic acid double-stranded and hybridized with the oligonucleotides on the nanoparticles resulting in the production of a triple-stranded complex.

In general, the nucleic acid can be any of a group of organic substances found in cells and viruses that play a central role in the storage and replication of hereditary information and in the expression of this information through protein synthesis. Purines, pyrimidines, carbohydrates, and phosphoric acid generally characterize the fundamental organic substances of a nucleic acid. Purines and pyrimidines are nucleotides, a nucleoside in which the primary hydroxy group of either 2-deoxy-D-ribose or of D-ribose is esterified by orthophosphoric acid. A nucleoside is a compound in which a purine or pyrimidine base is bound via a N-atom to C-1 replacing the hydroxy group of either 2-deoxy-D-ribose or of D-ribose, but without any phosphate groups. The common nucleosides in biological systems are adenosine, guanosine, cytidine, and uridine (which contain ribose) and deoxyadenosine, deoxyguanosine, deoxycytidine and thymidine (which contain deoxyribose). Thus, a purine base may be an adenine nucleotide or a guanine nucleotide. A pyrimidine base may be thymine nucleotide, a cytosine nucleotide, or a uracil nucleotide.

The sequence of a nucleic acid may be random or specific so as to encode a desired amino acid structure. For instance, a group of three nucleotides may comprise a codon. One codon comprises an amino acid. The coding region of a nucleic acid comprises codons.

The nucleic acid can exist freely, or can be bound to peptides or proteins to form nucleoproteins in discreet bundles or structured forms such as, for example, chromosomes. A nucleic acid also can exist in single-stranded or double-stranded forms. A nucleic acid may also be linear, circular, or supercoiled. Nucleic acid may be isolated directly from a cell or organelle. A plasmid or cloning vector are also examples of nucleic acids.

The nucleic acid can be made up of nucleotides, each containing a carbohydrate sugar (deoxyribose), a phosphate group, and mixtures of nitrogenous purine- and pyrimidine-bases. The sugar may be of a cyclic or acyclic form. DNA comprises only thymine and cytosine pyrimidines and no uracil. DNA may be isolated from a cell as genomic, nuclear, or mitochondrial DNA, or made synthetically, i.e., by chemical processes.

A gene present in a cell typically comprises genomic DNA made up of exonic and intronic stretches of DNA. The exonic stretches comprises nucleotides that comprise codons that encode amino acids, whereas the intronic stretches of DNA comprise nucleotides that likely do not comprise codons that encode amino acids. The nucleotide sequence of purines and pyrimidines determine the sequences of amino acids in the polypeptide chain of the protein specified by that gene.

DNA may also be isolated as complementary or copy DNA (cDNA) produced from an RNA template by the action of RNA-dependent DNA polymerase. For example, the cDNA can be about 100-800mer strands from PCR amplification. If the RNA template has been processed to remove introns, the cDNA will not be identical to the gene from which the RNA was transcribed. Thus, cDNA may comprise a stretch of nucleotides that are largely exonic in nature.

When in double-stranded form, the two DNA strands form a double helix. In this helix, each nucleotide in one strand is hydrogen bonded to a specific nucleotide on the other strand. Thus, in DNA, adenine bonds with thymine and guanine bonds with cytosine. The ability of nucleotides present in each strand to bind to each other determines that the strands will be complementary, e.g., that for every adenine on one strand there will be a thymine on the other strand.

RNA can be generally similar to DNA, but contains the sugar ribose instead of deoxyribose and the base uracil instead of thymine. RNA can be single-stranded or double-stranded and is transcribed from a cell's DNA. An RNA molecule may form a hairpin loop or other double-stranded structures. RNA may be template RNA, messenger RNA (mRNA), total RNA, or transfer RNA (tRNA). polysome. RNA-DNA hybrid molecules can be deposited according to the present invention. Furthermore, protein-nucleic acids, or "peptide nucleic acids" ("PNA") also may be used in accordance with the present invention.

The binding properties exhibited between complementary nucleotides makes nucleic acids useful as probes that can bind to other nucleic acids. Nucleic acids can be labelled and used as probes. By any one of a number of standard labelling techniques, nucleic acid probes can be used to detect, by hybridization, another nucleic acid. That hybridization can be visualized or detected if the label is, for example, a fluorescent, radioactive, or enzymatic label. Thus, a nucleic acid of the present invention also can be labelled, or modified so as to comprise a detectable entity, like a fluorescent marker or tag, a gold particle, streptavidin, digoxigenin, a magnetic bead, or other markers known to the skilled artisan. See, for example, U.S. Pat. No. 4,626,501 ("Labeled DNA") to Landes, which is hereby incorporated by reference.

Nucleotides and nucleic acids also can be modified so that it is protected against nucleic acid degradation. For instance, a nucleic acid may be encapsulated within a liposome. Alternatively, a thiol group may be incorporated into a polynucleotide, such as into an RNA or DNA molecule, by replacing the phosphorous group of the nucleotide. When so incorporated into the "backbone" of a nucleic acid, a thiol can prevent cleavage of the DNA at that site and, thus, improve the stability of the nucleic acid molecule.

U.S. Pat. No. 5,965,721 to Cook et al. is also incorporated by reference, disclosing oligonucleotides which can be patterned and can have improved nuclease resistance and improved cellular uptake.

Thus, the bioavailability of a nucleic acid treatment in vivo may be improved by modifying the nucleic acid as described. For instance, a modified nucleic acid formulation may have an increased half-life and/or be retained in plasma for longer periods of time than non-modified nucleic acids. A formulation of nucleic acid and polyethylene glycol, for instance, may also increase the half-life of the nucleic acid in vivo, as could any known slow-release nucleic acid formulation. Thus, modifying a nucleic acid may increase the effectiveness of the nucleic acid in vivo and/or its bioavailability.

The size of a nucleic acid can range considerably, from the size of a few nucleotides, to an oligonucleotide, or probe, to a polynucleotide, gene, chromosome fragment to entire chromosomes and genomes. For instance, a single- or double-stranded nucleic acid may be at least 10-, 20-, 30-, 40-, 50-, 60-, 70-, 80-, 90, or 100-nucleotides or base pairs (bp) in length. Larger still, a nucleic acid may be at least 0.2 kb, 0.3 kb, 0.4 kb, 0.5 kb, 0.6 kb, 0.7 kb, 0.8 kb, 0.9 kb, or 1.0 kb in size. Indeed, a nucleic acid for use in the present invention can be at least 1 kb, 2 kb, 3 kb, 4 kb, 5 kb, 6 kb, 7 kb, 8 kb, 9 kb, or 10 kb or larger in size. One preferred size range is 1-2 kb. The nucleic acid can be a chain of varying length of nucleotides and are typically called polynucleotides or oligonucleotides. An oligonucleotide is an oligomer generally resulting from a linear sequences of nucleotides. The oligonucleotide can comprise, for example, about 2 to about 100, about 2 to about 20, about 10 to about 90, or about 15 to about 35 nucleotides. In oligonucleotide arrays, about 25-mer oligonucleotides can be used. Another particular range is about 60- to about 80-mers, which are relatively long oligonucleotides.

Microarray methods, including selection of nucleic acid, probing, labeling, and detection, are described in U.S. Pat. Nos. 6,379,932 and 6,410,231 (Incyte Genomics) and can be used. These patents are incorporated by reference in their entirety. Although these references mention dip pen nanolithographic methods, they do not suggest how or provide guidance on how dip pen nanolithographic methods can be used to make improved nanoarrays as described herein.

A compound comprising a single nucleotide can also be used as ink. Mixtures of nucleic acids can be used, and different spots on an array can comprise different nucleic acids.

A nucleic acid for deposition according to the present invention may be formulated or mixed with other elements prior to, or after direct write deposition onto a substrate surface. Thus, an "ink" of the present invention may comprise other chemicals, compounds, or compositions for deposition onto a substrate surface in addition to a desired nucleic acid sample. As described above, solvent and salt can be used to apply the nucleic acid to the tips. Surfactants can be used. For instance, proteins, polypeptides, and peptides may be deposited along with a desired nucleic acid onto a substrate surface.

Nucleic acid arrays, and the types of nucleic acids used therein, are described for example in *A Primer of Genome Science*, G. Gibson and S. Muse, 2002, Chapters 3-4 (pages 123-181), which is hereby incorporated by reference. This reference, for example, describes both cDNA microarrays and oligonucleotide arrays, labeling, hybridization, and statistical analysis. cDNA arrays can be used for monitoring the relative levels of expression of thousands of genes simultaneously. PCR-amplified cDNA fragments (ESTs) can be spotted and probed against fluorescently or radioactively labeled cDNA. The intenstity of the signal observed can be assumed to be in proportion to the amount of transcript present in the RNA population being studied. Differences in intensity reflect differences in transcript level between treatments. Statistical and bioinformatic analyses can then be performed, usually with the goal of generating hypotheses that may be tested with established molecular biological approaches. Current cDNA microarrays, however, can have an upper limit of 15,000 elements and are unable to represent the complete set of genes present in higher eukaryotic genomes. The advantages and disadvantages of oligonucleotide versus cDNA microarrays are described in the aforementioned *A Primer of Genome Science* and can be used in constructing nucleic acid nanoarrays as described herein.

DIP PEN nanolithographic printing, particularly parallel DIP PEN nanolithographic printing, is useful for the preparation of nucleic acid nanoarrays, particular combinatorial nanoarrays. An array is an arrangement of a plurality of discrete sample areas, or pattern units, forming a larger pattern on a substrate. The sample areas, or patterns, may be any shape (e.g., dots, lines, circles, squares or triangles) and may be arranged in any larger pattern (e.g., rows and columns, lattices, grids, etc. of discrete sample areas). Pattern can refer to an individual unit or a larger collection of individual units. Each sample area may contain the same or a different sample as contained in the other sample areas of the array. A "combinatorial array" is an array wherein each sample area or a small group of replicate sample areas (usually 2-4) contain(s) a sample which is different than that found in other sample areas of the array. A "sample" is a material or combination of materials to be studied, identified, reacted, etc.

DIP PEN nanolithographic printing, particularly parallel DIP PEN nanolithographic printing, is particularly useful for the preparation of nanoarrays and combinatorial nanoarrays on the submicrometer scale. An array on the submicrometer scale, or nanoscale, means that at least one of the lateral dimensions (e.g, length, width or diameter) of the sample areas, excluding the depth, is less than 1 µm. These dimensions are lateral dimensions, generally in the plane of the substrate. DIP PEN nanolithographic printing, for example, can be used to prepare dots that are about 10 nm in diameter. With improvements in tips (e.g., sharper tips), dots can be produced that approach 1 nm in diameter. Arrays on a submicrometer scale allow for faster reaction times and the use of less reagents than the currently-used microscale (i.e., having dimensions, other than depth, which are 1-999 µm) and larger arrays. Also, more information can be gained per unit area (i.e., the arrays are more dense than the currently-used micrometer scale arrays). Finally, the use of submicrometer arrays provides new opportunities for screening. For instance, such arrays can be screened with SPM's to look for physical changes in the patterns (e.g., shape, stickiness, height) and/or to identify chemicals present in the sample areas, including sequencing of nucleic acids.

Each sample area of an array can contain a single sample or a single deposit. For instance, the sample may be a biological material, such as a nucleic acid as described extensively above (e.g., an oligonucleotide, DNA, or RNA), protein or peptide (e.g., an antibody or an enzyme), ligand (e.g., an antigen, enzyme substrate, receptor or the ligand for a receptor), or a combination or mixture of biological materials (e.g., a mixture of proteins or nucleic acids).

The present invention is particularly focused on nucleic acid, oligonucleotide, and DNA nanoarrays. Arrays and methods of using arrays are known in the art. For instance, such arrays can be used for biological and chemical screenings to identify and/or quantitate a biological or chemical material (e.g., immunoassays, enzyme activity assays, genomics, and proteomics). Biological and chemical libraries of naturally-occurring or synthetic compounds and other materials, including cells, can be used, e.g., to identify and design or refine drug candidates, enzyme inhibitors, ligands for receptors, and receptors for ligands, and in genomics and proteomics. Arrays of microparticles and nanoparticles can be used for a variety of purposes (see for example Example 7 of US Patent Publication 2002/0063212 A1). Arrays can also be used for studies of crystallization, etching (see for example Example 5 of US Patent Publication 2002/0063212 A1) and the like. References describing combinatorial arrays and other arrays and their uses include, for example, U.S. Pat. Nos. 5,747,334, 5,962,736, and 5,985,356, and PCT applications WO 96/31625, WO 99/31267, WO 00/04382, WO 00/04389, WO 00/04390, WO 00/36 136, and WO 00/46406, which are hereby incorporated by reference in their entirety. Finally, results of experiments performed on the arrays of the invention can be detected by conventional means (e.g., fluorescence, chemiluminescence, bioluminescence, and radioactivity). Alternatively, an SPM can be used for screening arrays. For instance, an AFM can be used for quantitative imaging and identification of molecules, including the imaging and identification of chemical and biological molecules through the use of an SPM tip coated with a chemical or biomolecular identifier. See, for example, Frisbie et al., *Science,* 265, 2071 2074 (1994); Wilbur et al., *Langmuir,* 11, 825-831 (1995); Noy et al., *J. Am. Chem. Soc.,* 117, 7943-7951 (1995); Noy et al., *Langmuir,* 14, 1508-1511 (1998); and U.S. Pat. Nos. 5,363,697, 5,372,93, 5,472,881 and 5,874,668, the complete disclosures of which are incorporated herein by reference.

Direct-write nanolithographic printing is particularly useful for the preparation of nucleic acid nanoarrays, arrays on the submicrometer scale having nanoscopic features, wherein a plurality of dots or a plurality of lines can be formed on a substrate. The plurality of dots can be a lattice of dots including hexagonal or square lattices as known in the art. The plurality of lines can form a grid, including perpendicular and parallel arrangements of the lines.

The lateral dimensions of the individual patterns including dot diameters and the line widths can be of a nanoscale, for example, about 1,000 nm or less, about 500 nm or less, about 300 nm or less, about 200 nm or less, and more particularly about 100 nm or less. The range in dimension can be for example about 1 nm to about 750 nm, about 10 nm to about 500 nm, and more particularly about 100 nm to about 350 nm. A small range of about 10 nm to about 100 nm can be used.

The number of patterns in the plurality of patterns is not particularly limited for a single substrate and generally high pattern density is desired. It can be, for example, at least 10, at least 100, at least 1,000, at least 10,000, even at least 100,000. Square arrangements are possible such as, for example, a 10×10 array. Higher density arrays are preferred, generally at least 100, preferably at least 1,000, more preferably, at least 10,000, and even more preferably, at least 100,000 discrete elements per square centimeter. Remarkably, the nanotechnology described herein can be used to generate ultra-high density nanoarrays comprising more than one million, more than 100,000,000, and more particularly, even more than one billion, discrete elements per square centimeter as a pattern density.

The distance between the individual patterns on the nanoarray can vary and is not particularly limited. For example, the patterns can be separated by distances of less than one micron or more than one micron. The distance can be, for example, about 300 to about 1,500 microns, or about 500 microns to about 1,000 microns. Distance between separated patterns can be measured from the center of the pattern such as the center of a dot or the middle of a line.

The amount of nucleic acid in a particular spot or deposit is not limited but can be, for example at a pg or ng level including, for example, about 0.1 ng to about 100 ng, and more particularly, about 1 ng to about 50 ng. Spotting solution methods used in nucleic acid microarray technology can be also used as desired in nanoarray technology.

By methods described herein, a nucleic acid nanoarray can be prepared comprising a substrate and a plurality of patterns of nucleic acid on the substrate, wherein the patterns of nucleic acid are chemisorbed or covalently bonded to the substrate, have lateral dimensions of about 1,000 nm or less and are separated from each other by distances of 1,000 nin or less, and are hybridizable to complementary nucleic acids. In a preferred embodiment, the nucleic acid nanoarray comprises at least 1,000 patterns of nucleic acid, wherein the lateral dimensions of the patterns are about 500 nm or less, the patterns are separated from each other by distances of 500 nm or less, and the patterns are in the form of dots. In another preferred embodiment, the nucleic acid nanoarray comprises at least 10,000 patterns of nucleic acid, wherein the lateral dimensions of the patterns are about 200 nm or less, the patterns are separated from each other by distances of 500 nm or less, and the patterns are in the form of dots.

Conventional substrates known for use with direct-write nanolithography and nucleic acid microarrays including glass can be used. In addition to those described above, substrates include membranes, plastic or polymeric gels, microwells, electrodes, nanogaps, and sensor devices. Membranes include those used in current nucleic acid microarray technology including nitrocellulose and nylon membranes. Substrates can be treated with, for example, a monolayer or a primer layer before the nucleic acid is deposited onto the substrate. The primer layer can be designed to covalently anchor the nucleic acid. For example, if 5'-aminoacylated PCR primers are used to amplify ESTs, aldehyde-based coatings can be used that link to the end of the nucleic acid molecules. Multi-layer architectures can be made.

In view of the rapid proliferation of bioconjugated nanoparticle labels and building blocks, the method described here should allow the DPN- and nucleic acid-templated assembly of a wide variety of metallic, semi-conducting, magnetic, and insulating nanostructures, on both metallic and insulating substrates. Exemplary publications include (1) M. Bruchez et al, Science, 281, 2013 (1998), (2) S. R. Nicewarner-Pena et al., Science, 294, 137 (2001); (3) Y. Cui, et al., Science, 293, 1289 (2001). These structures can in turn be used to address issues in molecular electronics, photonics, high-density information storage, and biosensing. The method also suggests new routes for investigating the fundamental limits of microarray miniaturization. With the resolution demonstrated here, arrays with ~100,000 nucleic acid or oligonucleotide spots could be generated in an area the size of a typical AFM scanner (100 µm by 100 µm) on time scales comparable with those of conventional robotic spotting methods, thereby making possible the investigation of scanned probe methods of nano- and microarray fabrication and readout. Robot methods, for example, can be limited by spotting rates of only a few deposits per second, which means it can take up to two days for robots to prepare 100 microarrays containing at least 5000 clones.

Nanoparticles useful in the practice of the invention include metal (e.g., gold, silver, copper, and platinum), semiconductor (e.g., CdSe, CdS, and CdSe or CdS coated with ZnS) and magnetic (e.g., ferromagnetite), colloidal materials. Other nanoparticles useful in the practice of the invention include ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_2As2$, InAs, and GaAs. The size of the nanoparticles is preferably from about 5 nm to about 150 nm (mean diameter), more preferably, from about 5 nm to about 50 nm, and more preferably, about 10 nm to about 30 nm. Methods of making and using nanoparticles bonded to nucleic acids are described in U.S. Pat. No. 6,361,944, which is hereby incorporated by reference.

The invention is further illustrated by the following working examples, which do not limit the scope of the invention as described in detail above and as claimed below.

WORKING EXAMPLES

The invention is further illustrated by the following non-limiting Experimental Section and Working Examples. In addition, Working Examples 1-7 in U.S. patent publication 2002/0063212 A1 to Mirkin et al. illustrate various embodiments for DIP PEN™ nanolithographic printing, and are hereby incorporated by reference.

Experimental Section

General methods and materials. 1-Octadecanethiol was purchased from Aldrich (Milwaukee, Wis.). Thiol-modified 15-mer DNA with a polyethyleneglycol spacer ($PEG_6$) corresponding to 18 atoms between the anchor groups and DNA (C1, C2, see Table I) was purchased from IDT (Coralville, Iowa, PAGE purified) and used without further purification. Linking DNA (L1 and L2) and gold nanoparticle-bound DNA (G1) used in gold substrate patterning experiments were synthesized as previously reported (see, for example, J. J. Storhoff et al., J. Am. Chem. Soc., 120, 1959 (1998); and U.S. Pat. Nos. 6,417,340 and 6,361,944 to Mirkin et al.).

Acrylamide modified (Acrydite™) 12- and 15-mer DNA (C3 and C4) were purchased from IDT (RP HPLC purified). Linking DNA (L3 and L4) and nanoparticle-bound DNA (G2 and G3) used in silicon oxide patterning experiments were synthesized by known methods (see, for example, J. J. Storhoff et al., J. Am. Chem. Soc., 120, 1959 (1998); and U.S. Pat. Nos. 6,417,340 and 6,361,944 to Mirkin et al.).

TABLE I

Oligonucleotide sequences used for DPN patterning, nanoparticle modification, and linking of particles to DNA-patterned surfaces.

| Strand Name | Sequence and End Modifications | SEQ ID NO: |
|---|---|---|
| C1 | 5'HS$(CH_2)_6$-$PEG_6$-GAG GGA TTA TTG TTA | 1 |
| C2 | 5'HS$(CH_2)_6$-$PEG_6$-AGT CGC TTC TAC CAT | 2 |
| L1 | 5'AGA GTT GAG CTA TAA CAA TAA TCC CTC | 3 |
| L2 | 5'AGA GTT GAG CTA ATG GTA GAA GCG ACT | 4 |
| G1 | 5'TAG CTC AAC TCT $A_{20}(CH_2)_3$SH | 5 |
| C3 | 5'Acrydite-$PEG_6$-ATC CTT ATC AAT ATT | 6 |
| C4 | 5'Acrydite-$PEG_6$-CGC ATT CAG GAT | 7 |
| L3 | 5'GGA TTA TTG TTA AAT ATT GAT AAG GAT | 8 |
| L4 | 5'TAC GAG TTG AGA ATC CTG AAT GCG | 9 |
| L3F | Oregon Green488X-5'GGA TTA TTG TTA AAT | 10 |
| L4F | Oregon Green488X-5'TAC GAG TTG AGA | 11 |
| G2 | 5'TCT CAA CTC GTA $A_{10}(CH_2)_3$SH | 12 |
| G3 | 5'TAA CAA TAA TCC $A_{10}(CH_2)_3$SH | 13 |

Gold thin films on single crystalline silicon wafers were prepared according to previously reported procedures (see L. M. Demers et al., Anal. Chem. 72, 5535 (2000). Silicon oxide substrates were cleaned in piranha solution (3:1 sulfuric acid to 30% hydrogen peroxide) prior to silanization with mercaptopropyltrimethoxysilane (MPTMS) for 2 h by vapor transport (see for example D. G. Kurth et al. Langmuir, 9, 2965 (1993), after which they were rinsed with ethanol and cured under flowing $N_2$ for 10 min at 80° C.

AFM tip preparation. Conventional silicon nitride probe chips (spring constant ~0.3 $Nm^{-1}$, Thermomicroscopes, Sunnyvale, Calif.) were first cleaned for 10 min in piranha solution ($1H_2O_2$: $3H_2SO_4$), rinsed with DI water, ethanol, and toluene, and then immersed in a 1% vol/vol solution of 3-aminopropyltrimethoxysilane (APS) in toluene in a glass petri dish for 1-2 h. After silanization the chips were rinsed with toluene, and then dried under a stream of nitrogen. In a typical procedure, tips were coated immediately with thiol-modified DNA by dipping in tip coating solution (1 mM DNA, 90% dimethylformamide (dmf), 10% water, 0.3 M $MgCl_2$) for 20 s and subsequently drying with compressed difluoroethane. Amine-coated tips were well coated with dimethylformamide (DMF) solutions of DNA if dipped immediately into the solution after silanization, but in general only poorly coated after 12 h, presumably due to contamination of the tip surface.

Dip-Pen Nanolithographic Printing experiments. Dip-pen nanolithographic printing was performed using DNA-coated AFM tips (contact force ~2.5 nN) in a controlled atmosphere glovebox. The glovebox enabled control over temperature and humidity to within ±5° C. and ±5% relative humidity. All DPN printing experiments were performed using a Park Scientific Instruments Autoprobe CP AFM with a customized DPN printing software interface.

Gold nanoparticle assembly. Gold nanoparticles were modified with thiol-functionalized DNA by known methods (see, for example, J. J. Storhoff et al., *J. Am. Chem. Soc.,* 120, 1959 (1998); and U.S. Pat. Nos. 6,417,340 and 6,361, 944 to Mirkin et al.). For assembly onto patterned gold substrates, nanoparticles (20 μl, 13 nm diameter, 5 nM) modified with thiol-capped DNA were hybridized overnight to linking DNA for at least 12 h in hybridization solution (final concentrations 0.1 μM DNA, 0.3 M PBS (0.01 M phosphate buffer pH 7, 0.3 M NaCl), 0.025% sodium dodecyl sulfate (SDS)). The particle-DNA solution was then placed as a droplet on the horizontal patterned substrate and incubated at room temperature for 3 h. Following incubation, the slide was placed in a polypropylene tube and rinsed under a stream of buffer at room temperature (0.3 M PBS, 0.025% SDS), followed by 0.3 M ammonium acetate, pH 7, to remove salt from the surface to prepare the slide for AFM imaging. For particle assembly onto DNA-patterned SiOX substrates, linker DNA was hybridized to DNA-modified nanoparticles (0.5 μM linker, 10 nM particles, total volume 0.2 ml) by heating to 60° C. for 5 min, then allowing to cool for 30 min. The solution was subsequently diluted to 1 ml total volume with 0.3 M PBS 0.025% SDS and used for hybridization to patterned substrates as described above.

Imaging experiments. Tapping mode topography and phase AFM images of DNA patterns and nanoparticles were obtained using a Digital Instruments (Santa Barbara, Calif.) Nanoscope IIIa with silicon cantilevers from Digital Instruments, spring constant ~40 $Nm^{-1}$. All AFM images were processed only by applying first or second order flattening function. For fluorescence imaging the patterned substrates were hybridized at room temperature with fluorophore-labeled, complementary DNA for 30 min. in 2×SSPE buffer (2 μM DNA, 0.3 M NaCl, 0.02 M sodium phosphate, 0.002 M EDTA, 0.2% SDS, pH 7.4), rinsed with 2×SSPE 0.2% SDS and then immersed in 2×SSPE 0.2% SDS for 10 min. The substrates were rinsed with 0.3 M ammonium acetate and blown dry with $N_2$ prior to fluorescence imaging with a Zeiss Axiovert 100 microscope with a Hg lamp white light excitation source.

Example 1

Patterning of Nucleic Acid by Dip Pen Nanolithographic Printing

This example describes a method of patterning nucleic acids by DPN printing which provides improvements in tip-coating, diffusion to the substrate surface, and pattern stability during post-processing steps. This method employs an aminosilane-modified silicon nitride AFM cantilever-tip assembly and cyclic disulfide and polyethyleneglycol modified synthetic nucleic acid to form stable oligonucleotide patterns on a gold substrate, which can be hybridized with probes including, for example, nanoparticle probes. Judicious selection of relative humidity during printing provides for control of the size of the printed features.

1. AFM Tip Pretreatment Procedure

A conventional silicon nitride AFM tip was first modified with trimethoxyamino-propylsilane (APS). The cantilevers were cleaned in piranha etch (3:1 concentrated sulfuric acid/30% hydrogen peroxide) for 10 minutes, then rinsed in Nanopure water, and ethanol and dried in a stream of nitrogen. Tips were then covalently modified by immersion in 1% solution of APS in toluene for 1 hour, and then rinsed with toluene. This procedure created a positively-charged surface to which the negatively-charged nucleic acids adhered.

2. AFM Tip Coating

A 1 mM solution of modified synthetic DNA, containing (a) either a single hexanethiol moiety or a cyclic disulfide epiandrosterone linker and (b) a polyethylene glycol (PEG) spacer (see FIGS. 1 and 3), was prepared in 20 microliters of dimethylformamide (DMF) and 1 microliter of 1.5 M $MgCl_2$ in water. Pretreated AFM tips were coated with DNA by dipping the tips in the solution for 20-60 seconds (s) and blowing dry with compressed air or nitrogen. In general, the DMF plays a role in solubilizing the DNA and can allow wetting of the APM tip with the coating solution. In general, the low concentration of $MgCl_2$ was used to achieve high density DNA patterns on a surface by screening repulsive interactions between DNA strands. In general, the PEG spacer can be important in providing diffusion of the DNA to the substrate.

3. Direct Patterning of DNA via DPN Printing

Figure 3:
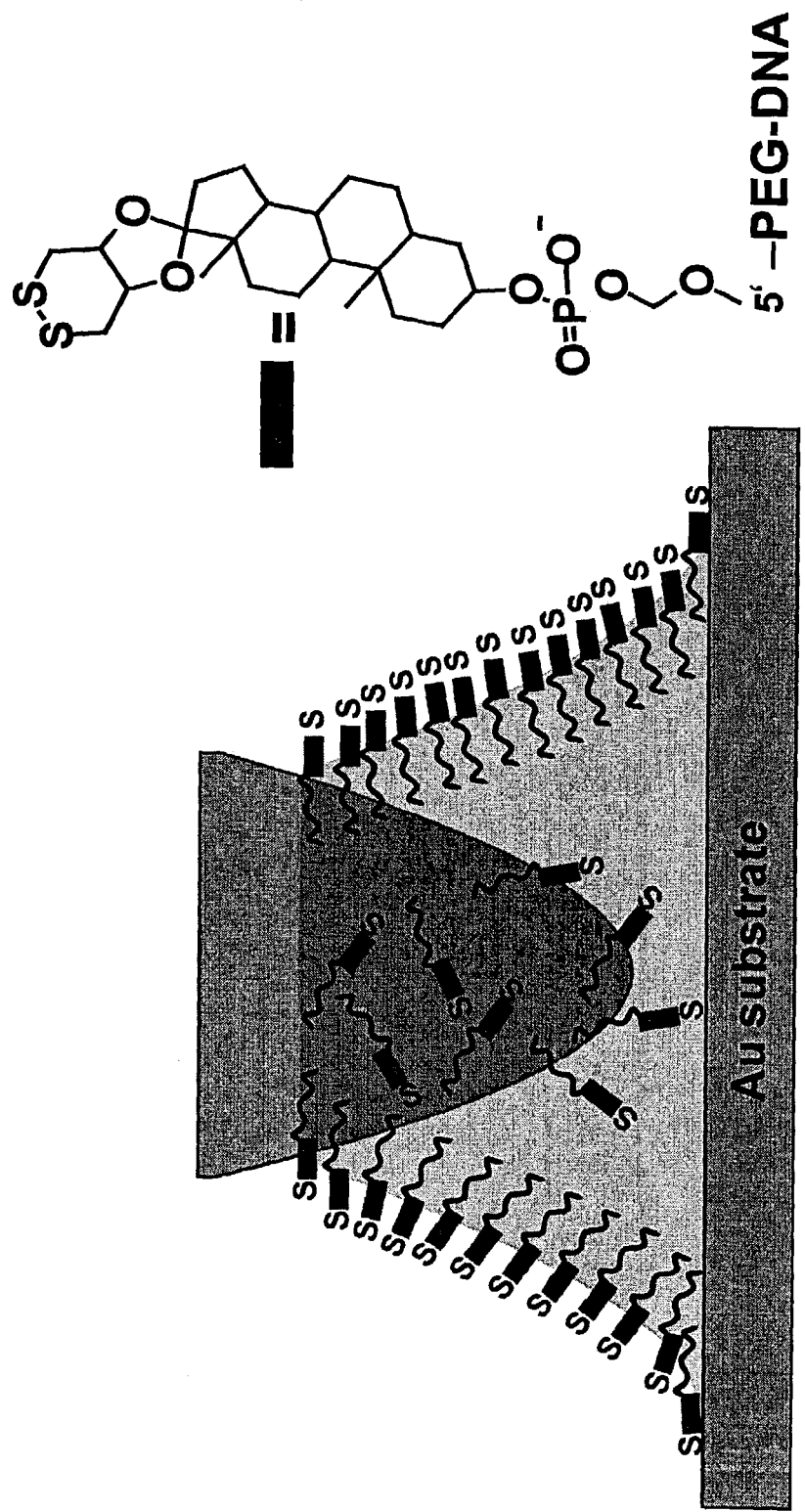
FIG. 3 illustrates transport of cyclic disulfide-modified DNA to a gold substrate from a coated AFM tip.
Figure 4:
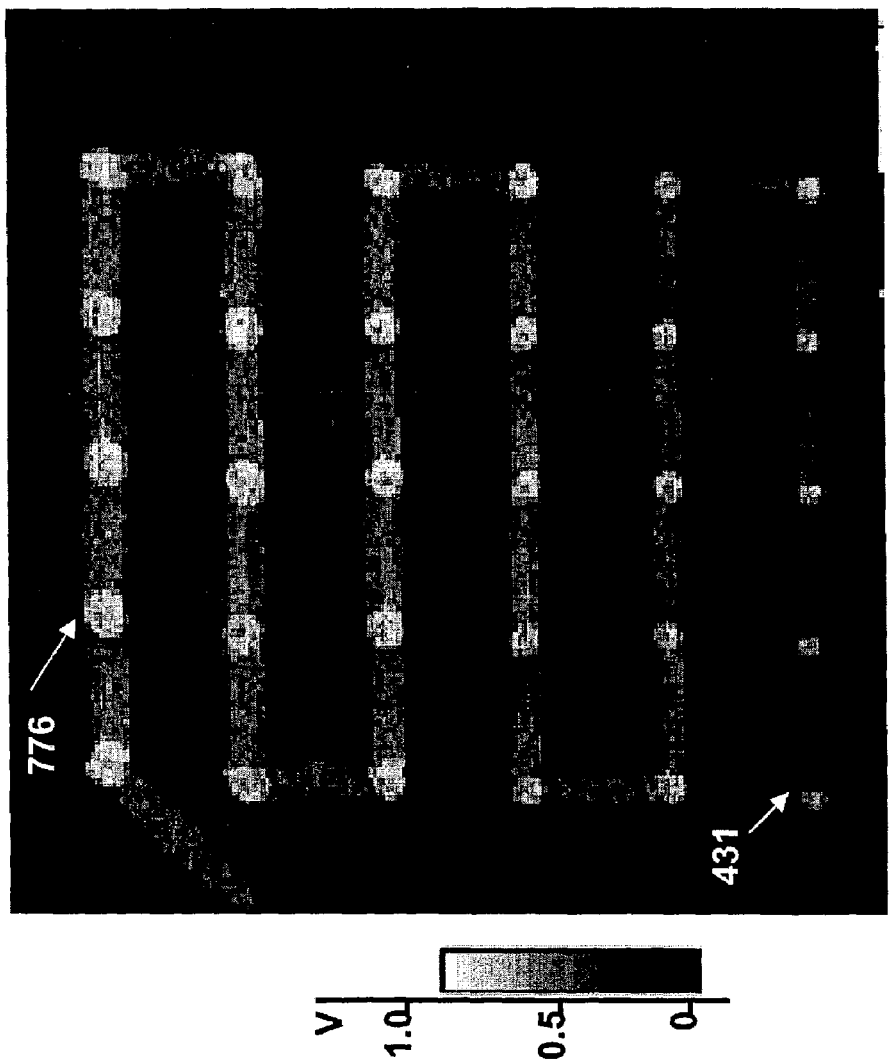
FIG. 4 illustrates lateral force microscopy images of DNA patterns. Control over DNA pattern size was achieved by varying relative humidity in an atmospheric control chamber
Figure 5:
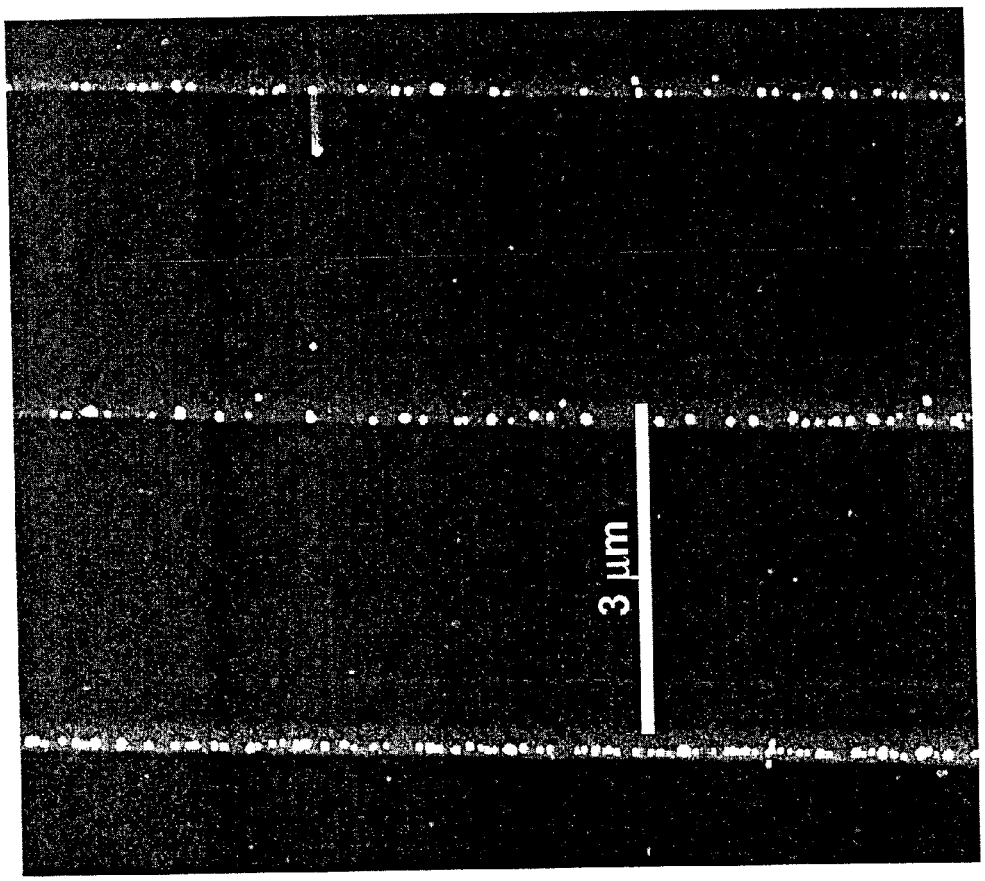
FIG. 5 illustrates a tapping mode AFM image of DNA patterns generated on gold via DPN (lines) and 13 mm gold nanoparticles assembled onto the patterns via specific DNA hybridization interactions.

To transfer DNA to a gold substrate, the DNA-coated AFM tip was positioned relative to the substrate and brought close to the substrate so as to be in contact with the substrate (see FIG. 3). Tip movement along the surface was controlled by DPN printing software. Control over pattern size was achieved by varying the relative humidity in an atmospheric control chamber. For example, the diameter of dot patterns could be varied from about 780 nm at about 88% relative humidity (upper row) to about 430 nm at about 50% relative humidity (lower row; see FIG. 4—All dots were made by holding the AFM tip in position for 20 seconds.) The disulfide linker forms a chelate bond to the gold surface which increases the stability of the DNA binding to the surface. DNA bound in this way resists displacement by alkanethiols (such as 1-octadecanethiol) which are used for passivation of the surrounding unpatterned gold. The DNA patterns were shown to have biological activity by hybridization to gold nanoparticle probes which had been modified with complementary DNA sequences (see FIG. 5 and see, for example, Letsinger, R. L, Elghanian, R.; Viswanadham, G.; Mirkin, C. A. *Bioconjugate Chemistry,* 2000, 11, 289-291; and PCT application WO 98/04740.

Examples 2 and 3

The use of direct-write dip-pen nanolithography printing (e.g., DPN printing) to generate covalently anchored, nanoscale patterns of oligonucleotides on metallic, conductive substrates such as gold (Ex. 2) and insulating substrates (Ex. 3) was carried out. Modification of DNA with hexanethiol groups provided for patterning on gold (Ex. 2), and oligonucleotides bearing 5'-terminal acrylamide groups were patterned on derivatized silica (Ex. 3). Feature sizes ranging from many micrometers to less than 100 nanometers were achieved in these examples, and the resulting patterns exhibited the sequence-specific binding properties of the DNA from which they were composed. The patterns were used to direct the assembly of individual oligonucleotide-modified particles on a surface, and the deposition of multiple DNA sequences in a single array was demonstrated.

DPN printing was used to pattern oligonucleotides on gold (Ex. 2) and silicon oxide (Ex. 3) surfaces. Several keys were identified that facilitated DNA patterning. First, the AFM tip was well coated with DNA. Although unmodified silicon nitride cantilevers have been used to deposit a variety of hydrophobic molecules by DPN, such cantilevers can yield DNA patterns with feature sizes and shapes that at times are controlled with difficulty. Improved control over DNA patterning was achieved through surface modification of a silicon nitride AFM cantilever with 3'-aminopropyltrimethoxysilane (for 1 hour in a 1% v/v solution in toluene), which promoted reliable adhesion of the DNA ink to the tip surface.

The silanized tips were coated with DNA by dipping them for 10 s into a 90% dimethylformamide/10% water solution containing 1 mM DNA and 0.3 M $MgCl_2$ and then the tips were blown dry with compressed difluoroethane. The positively charged hydrophilic tip surfaces were readily wetted by this DNA ink solution, and these AFM tips could be used in DPN printing experiments for several hours before they were recoated. The tips were also successfully used by coating them with an evaporated gold layer and a self-assembled monolayer of cysteamine. Furthermore, it was found that control of ambient humidity enabled reliable DPN patterning of oligonucleotides. Unless specifically noted, all patterning was performed in an environmentally controlled glovebox at a relative humidity of 45±5% at 23±3° C.

Figure 6:
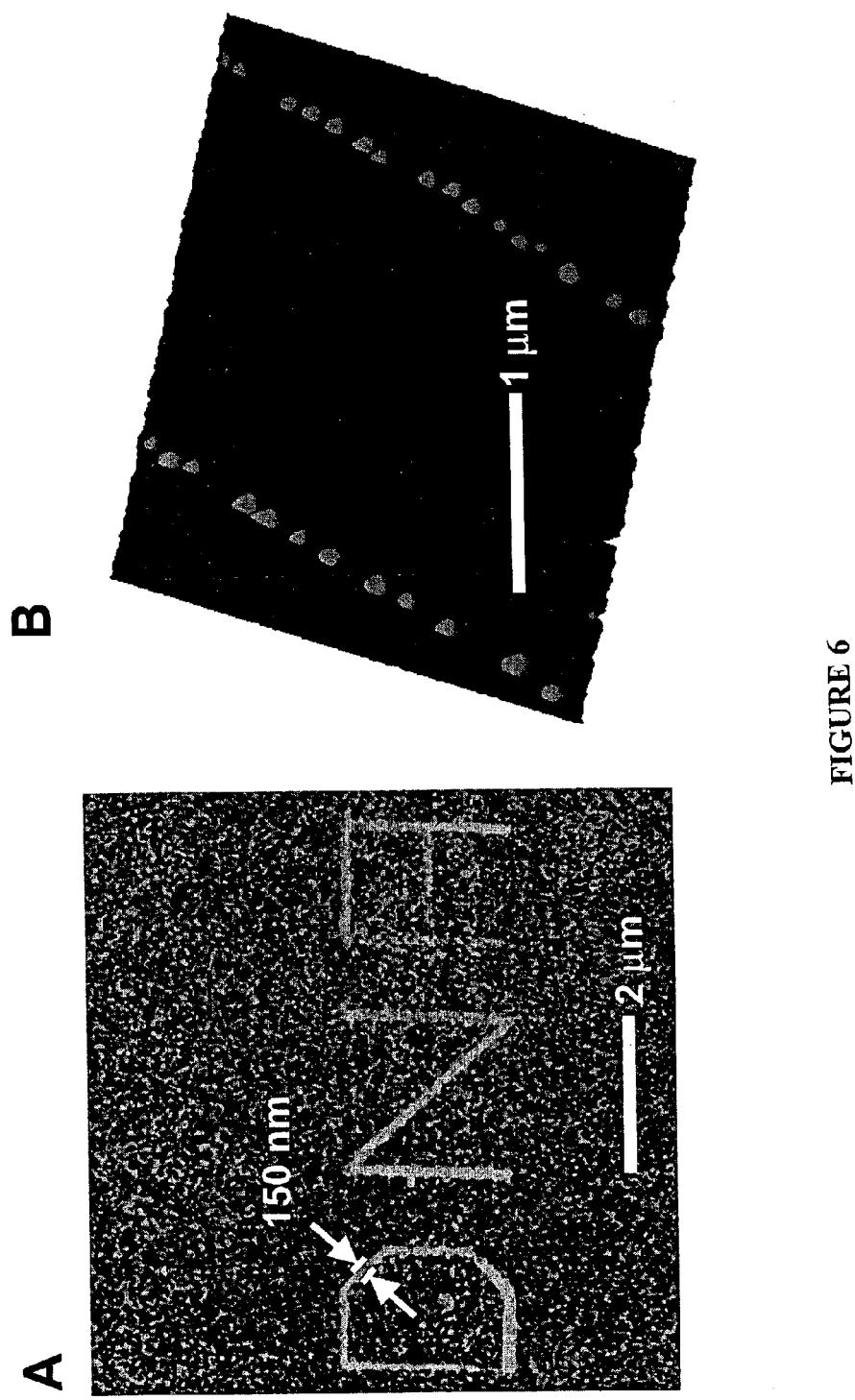
FIG. 6 illustrates direct transfer of DNA onto gold substrates by DPN printing. (A) Tapping-mode AFM image of hexane-thiol-modified oligonucleotides patterned on polycrystalline gold. The scale bar represents 2 microns, and the space between the arrows is 150 nm. (B) Tapping-mode AFM images of single oligonucleotide-modified gold nanoparticles (13 nm diameter) bound to a high resolution DNA line on gold by Watson-Crick base pairing in the presence of complementary linking DNA. The scale bar represents one micron.
Figure 7:
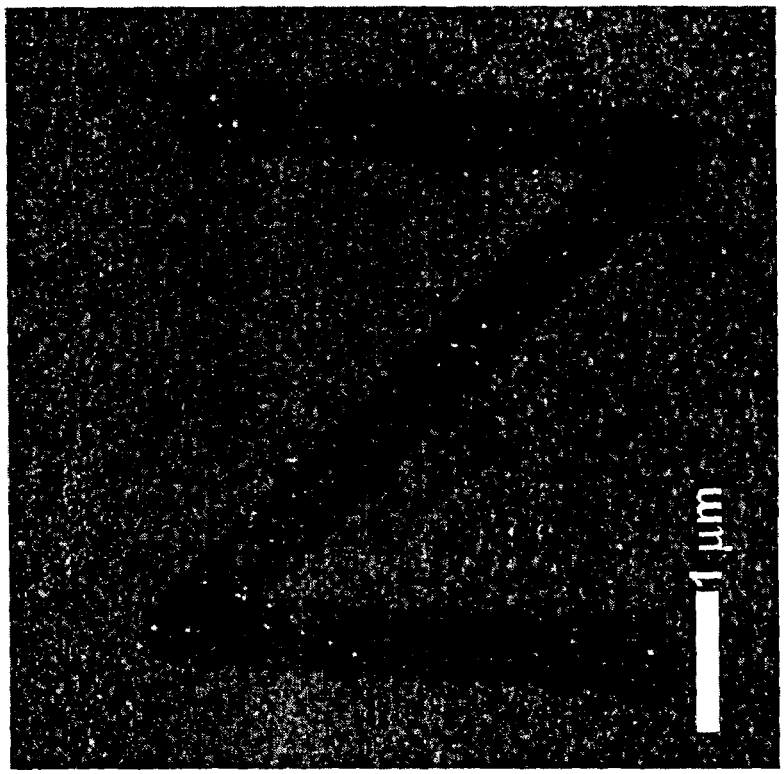
FIG. 7 illustrates tapping-mode AFM phase image of hexanethiol-modified oligonucleotides patterned on polycrystalline gold after exposure to oligonucleotide-modified gold nanoparticles (13 nm diameter) prehybridized to a 24-base linker sequence which was not complementary to the patterned DNA.
Figure 8:
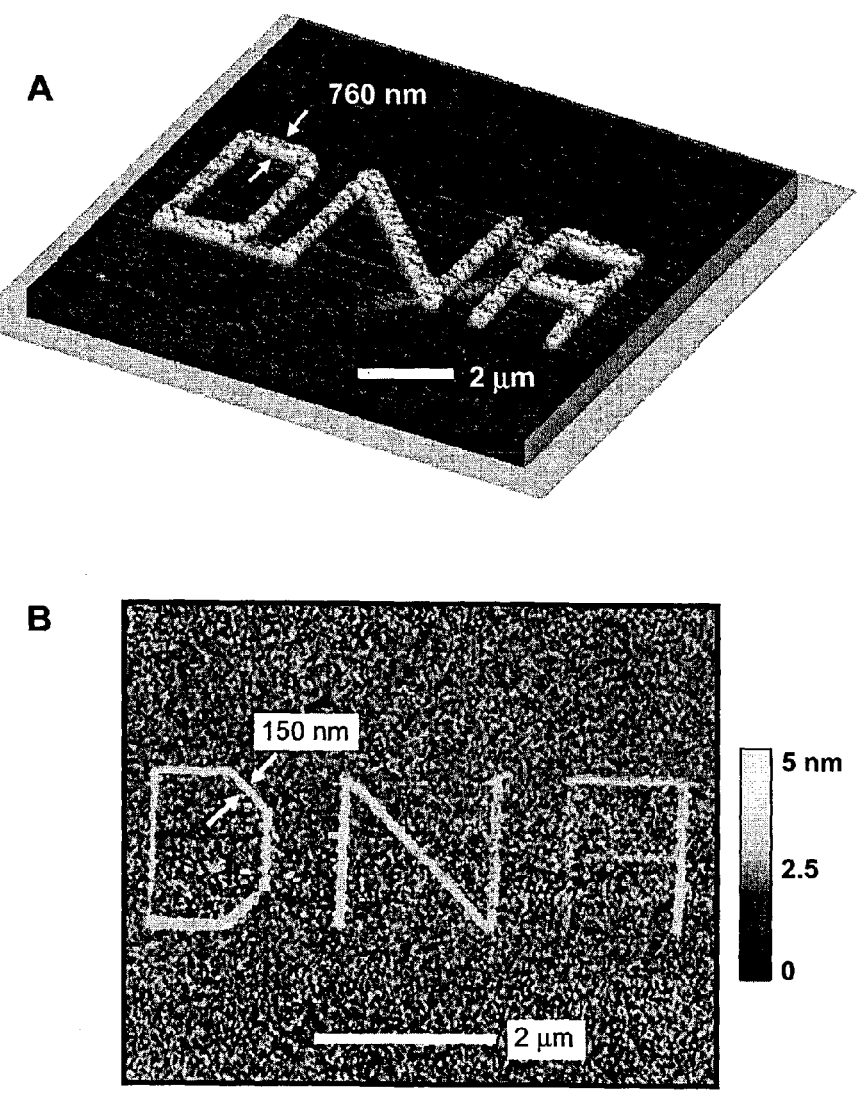
FIG. 8 illustrates direct transfer of hexanethiol-modified oligonucleotides onto polycrystalline gold substrates via DPN printing. (A) Lateral force atomic force micrograph of patterned surface after ODT treatment, (B) tapping-mode AFM image of a DNA pattern after ODT treatment.
Figure 9:
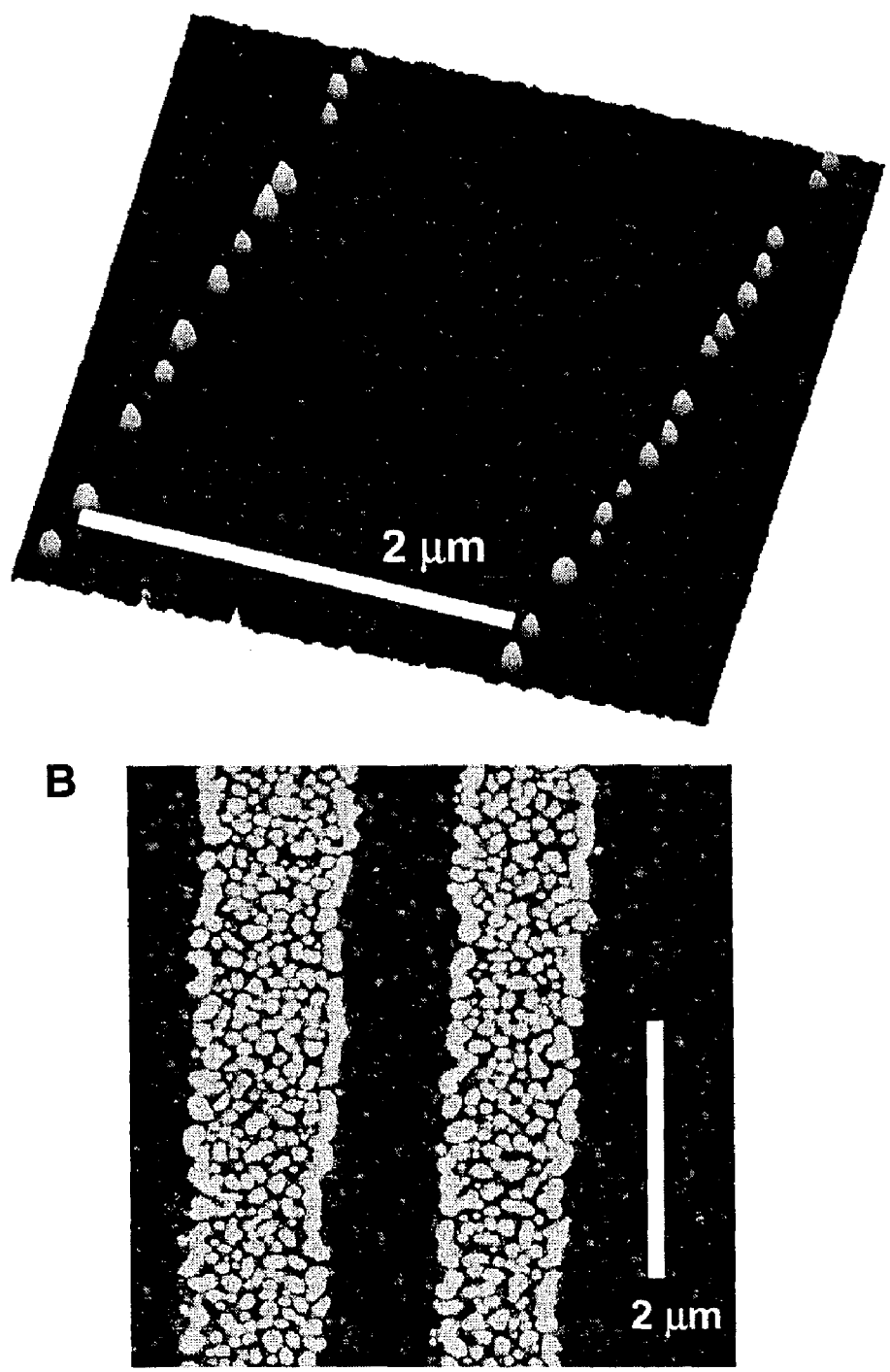
FIG. 9 illustrates tapping-mode AFM image of (A) single G1-modified gold nanoparticles (13 nm diameter) bound to DNA lines (50 nm wide) of C1 on gold via Watson-Crick base pairing in the presence of complementary linking DNA, L1 (B) G1-modified gold nanoparticles bound to thick DNA lines via hybridization in the presence of L1.

The judicious choice of an ink-substrate combination also facilitated the DPN printing process. In Example 2, for example, hexanethiolmodified oligonucleotides were used to directly pattern gold substrates with features ranging from 50 nm to several micrometers in size (FIGS. 6-10). It is generally believed that the hexanethiol group of the DNA chemisorbs to the underlying Au surface (see, for example, T. M. Herne et al., *J. Am. Chem. Soc.*, 119, 8916 (1997). After the substrates were patterned with oligonucleotides, they were immersed in an ethanol solution of 1-octadecanethiol (ODT, 1 mM) for 1 minute. This procedure coated the unpatterned gold surface with a hydrophobic monolayer, passivating it toward the nonspecific adsorption of DNA, or DNA-modified nanoparticles, in subsequent hybridization experiments. After the ODT treatment of the substrate, the oligonucleotide patterns were imaged by tapping-mode AFM and exhibited feature heights of 2 to 5 nm (FIG. 6A). See, R. Levicky et alt. *J. Am. Chem. Soc.*, 120, 9787 (1998). The immobilized DNA retained its highly specific recognition properties, and the patterns could be used to direct the assembly of 13-nm-diameter oligonucleotide-modified gold nanoparticles (FIG. 6B). Structures were fabricated by this process on the many micrometer to sub-100-nm-length scale, and individual particles were placed on a surface in the form of a preconceived architecture (FIGS. 6-9). The interactions between the DNA nanopatterns and the oligonucleotide-modified nanoparticles were highly selective; in the absence of a complementary linking strand, there was almost no nonspecific binding (FIG. 7).

Figure 10:
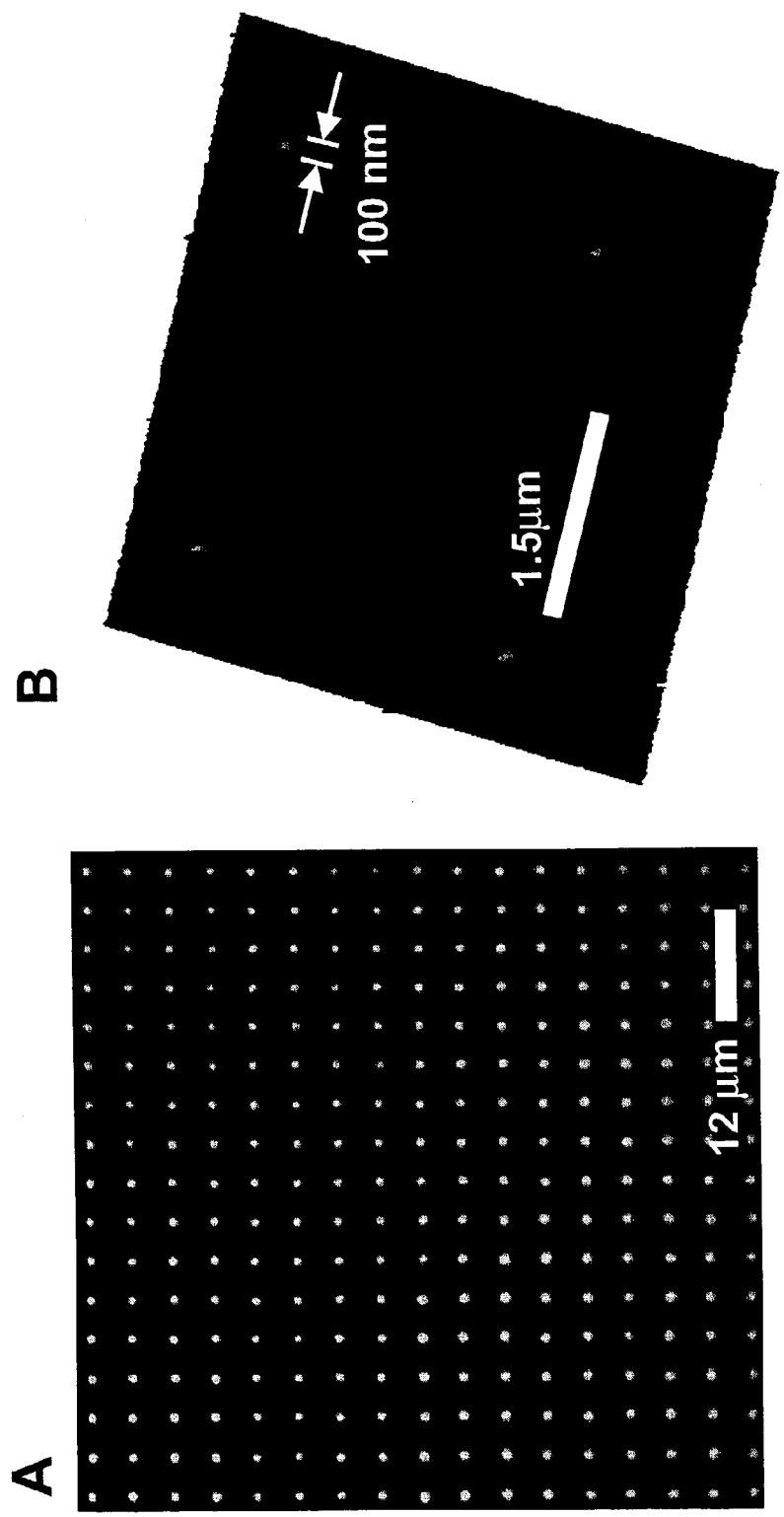
FIG. 10 illustrates direct DPN transfer of DNA onto insulating substrates. (A) Epifluorescence micrograph of fluorophore-labeled DNA (Oregon Green 488-X) hybridized to a DPN-generated pattern of complementary oligonucleotides on an $SiO_x$ surface. The scale bar represents 12 microns. (B) Tapping-mode AFM image of oligonucleotide-modified gold nanoparticles (13 nm diameter) hybridized to a second, high resolution pattern after removal (using DI water) of the fluorophore-labeled DNA. The scale bar represents 1.5 microns, and the space between the arrows is 100 nm.
Figure 11:
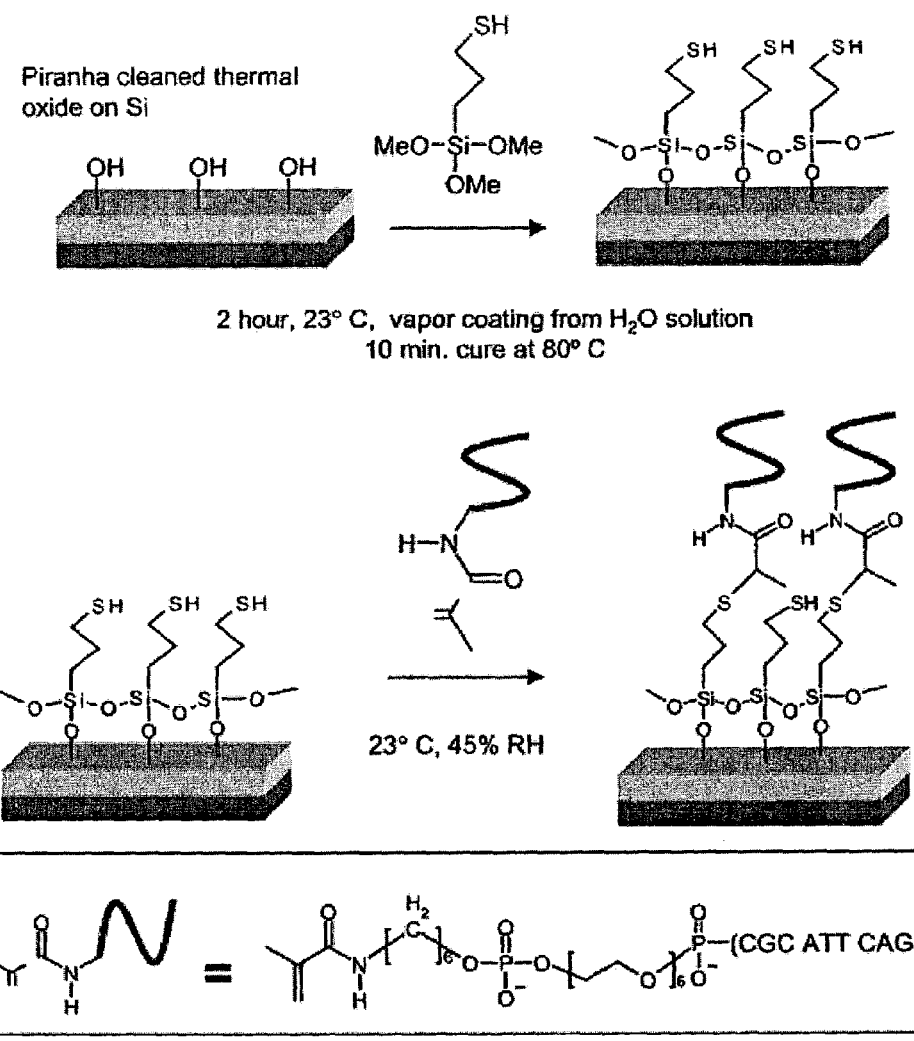
FIG. 11 illustrates a scheme for the DPN printing functionalization of SiOx substrates. (A) Silicon wafers are treated with 3-mercaptopropyltrimethoxysilane, (B) a DNA coated AFM tip delivers acrylamide modified DNA to the substrate during a brief contact (seconds).

Although the gold-thiol system provided an excellent method for patterning oligonucleotides using DPN printing, the electrical conductivity of the gold substrate prevents the study of charge transport and near-field optical phenomena in nanostructures assembled on such surfaces and also quenches the emission from any surface-bound fluorophores. Thus, DPN printing methods were developed to generate patterns of DNA on oxidized silicon wafers (FIG. 10). The surface of a thermally oxidized wafer was activated by treatment with 3'-mercaptopropyltrimethoxysilane (MPTMS). See, D. G. Kurth et al., *Langmuir*, 9, 2965 (1993). The preparation and inking of the AFM tip were performed substantially the same as for the patterning of DNA onto gold surfaces, but in this case, oligonucleotides with 5'-terminal acrylamide groups were used. See, M. Kenney, *Biotechniques*, 25, 516 (1998). Under the DPN printing conditions of room temperature and 45% relative humidity, the acrylamide moieties react by Michael addition with the pendant thiol groups of the MPTMS to covalently link the DNA to the surface (see FIG. 11). After patterning, the substrate was passivated by reaction with buffered acrylic acid monomer at pH 10 (Apogent Discoveries Quench Solution, 30 mm). After all DNA spots and sequences have been patterned, the substrate was typically left overnight to allow the formation of the thioether adduct before the substrate was washed and the unreacted thiol groups in the unpatterned areas are quenched. The biological activity of the patterned oligonucleotides was verified by exposing the surface to a solution containing both complementary and noncomplementary fluorophore-labeled DNA. The patterns were subsequently characterized by epifluorescence microscopy (FIG. 10A). In all cases, only fluorescence corresponding to the complementary target and the patterned area was detected. The same DNA nanostructures [after dehybridization of the single-stranded complement by rinsing with deionized (DI) water] could be used to direct the assembly of complementary DNA-modified gold nanoparticles (FIG. 10B). With this technique. DNA spots were generated and detected with diameters of 50 nm, nearly 160,000 times smaller (in terms of areal density) than those in conventional microarrays.

Example 4

Figure 12:
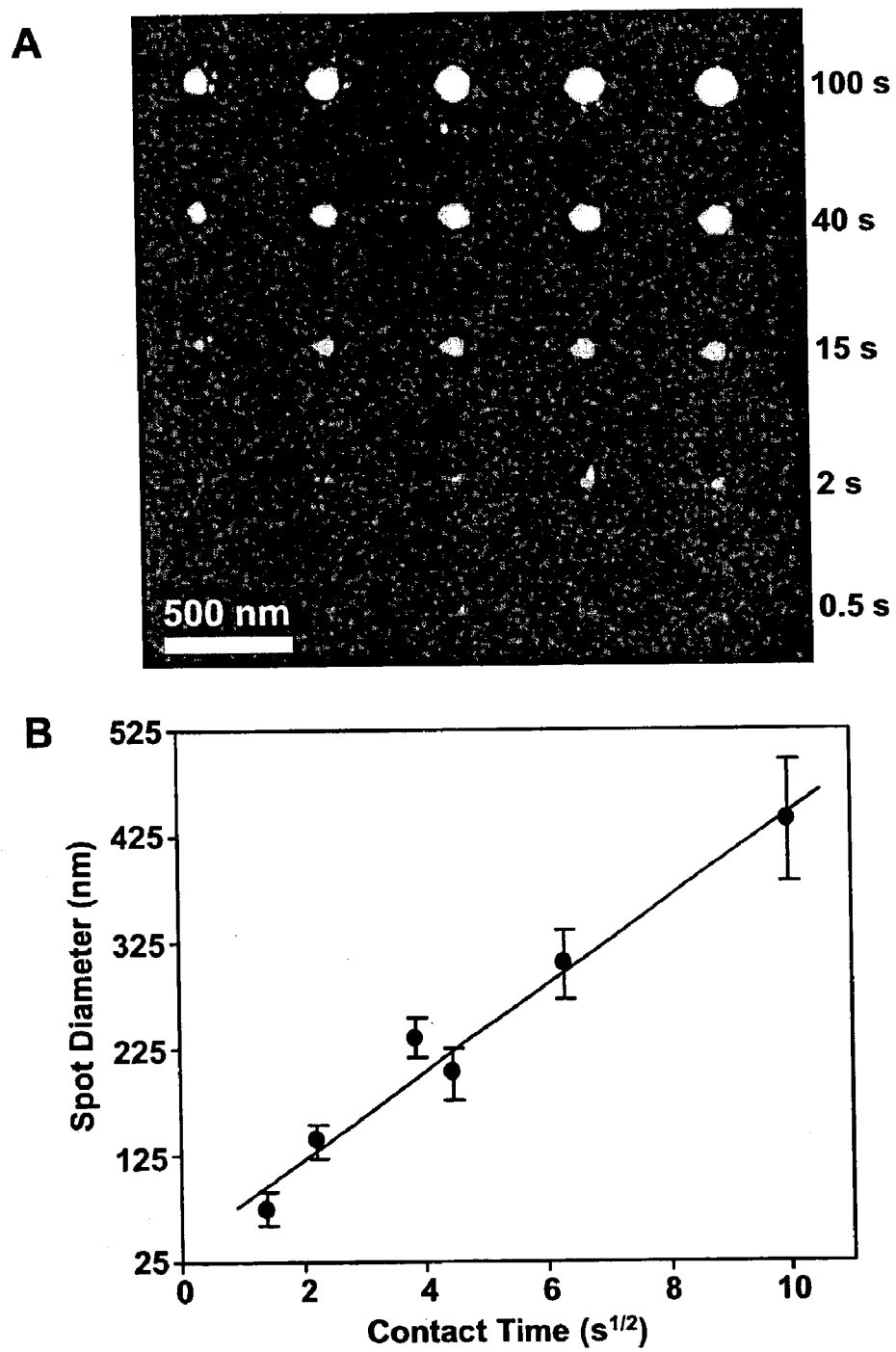
FIG. 12 illustrates DPN printing control over deposited DNA feature size. (A) Tapping-mode AFM image of thiol-modified DNA deposited on a gold substrate for different tip contact times at 45% relative humidity. (B) Spot diameter (from A and duplicate experiments) plotted vs. square root of contact time. Error bars were calculated from the standard deviation of at least 5 points.
Figure 13:
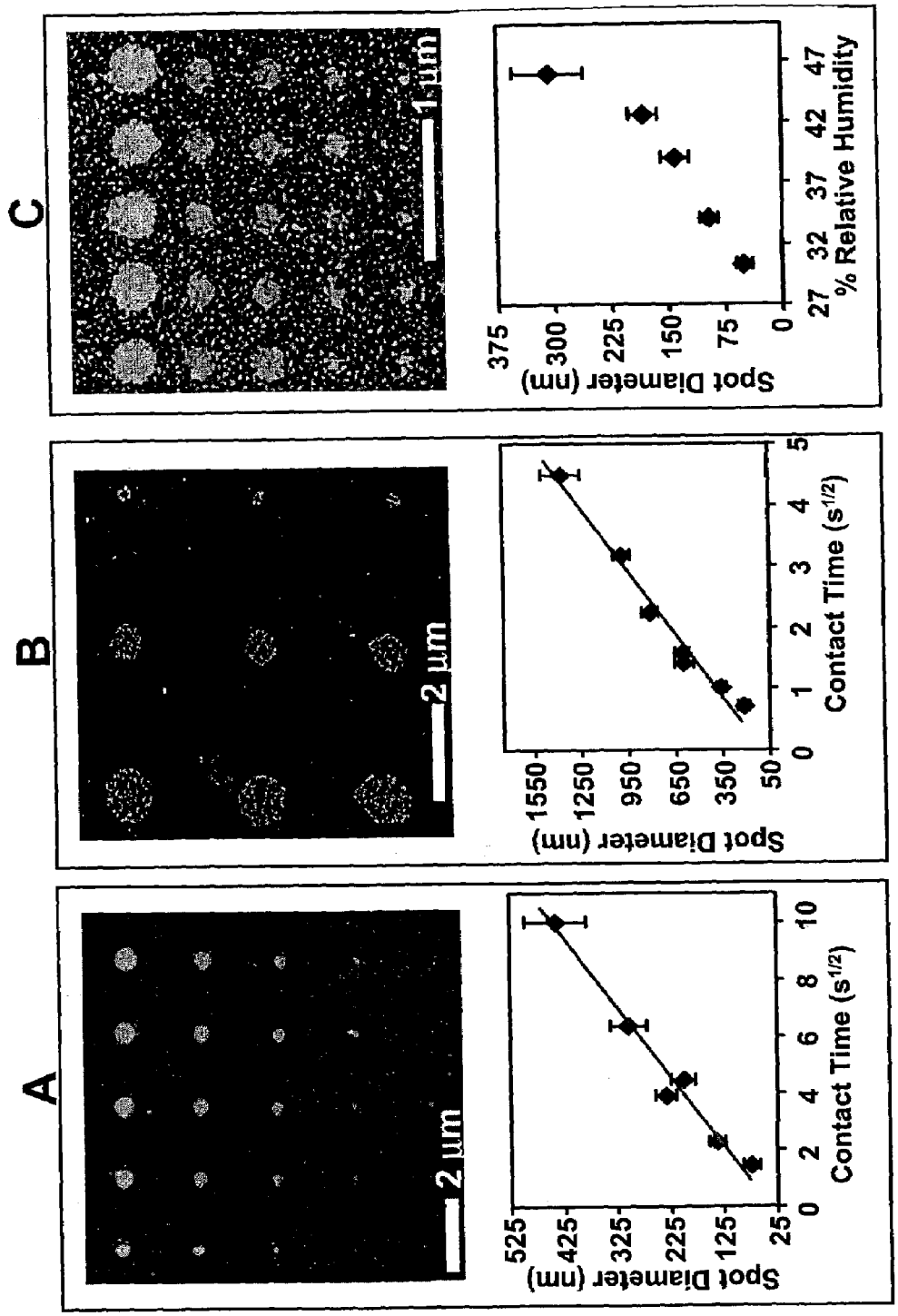
FIG. 13 further illustrates DPN printing control over deposited feature size. (A) Tapping-mode AFM image of thiol-modified DNA spotted on a gold substrate for different contact times at 45% relative humidity (top) and plot of dot diameter versus square root of contact time (bottom). (B) Tapping-mode AFM image of nanoparticles hybridized to DNA spots formed on $SiO_x$ for different contact times at 45% relative humidity (top) and plot of dot diameter versus square root of contact time (bottom). The scale bars for (A) and (B) represent 2 microns. (C) Tapping-mode AFM image of DNA spots generated on polycrystalline Au with contact time of 10 s per spot, at varying relative humidity (top), and a plot of spot diameter versus relative humidity (bottom). The scale bar represents 1 micron. Error bars for all plots were calculated from the standard deviation of at least five points.

An important feature of DPN printing is the ability to generate patterns of specific chemical functionality over a large range of length scales while exhibiting control over feature size in a preconceived manner. Surprisingly, patterns of highly charged macromolecules such as oligonucleotides can be transferred to a substrate in much the same way as can small hydrophobic molecules. On both gold and MPTMS-modified silicon oxide substrates, the transport of DNA from the AFM tip to the surface followed the same linear increase in pattern area with contact time predicted theoretically (see, J. Jang et al, *J. Chem. Phys.*, 115, 2721 (2001)), as well as observed for alkanethiols on gold (see D. A. Weinberger et al., *Adv. Mater.*, 12, 1600 (2000) and for silazanes on silicon and gallium arsenide (see, Maynor et al., *Langmuir*, 17, 2575 (2001), (FIGS. 12 and 13A,B). Although the rate constants can be different for each ink-substrate pair, this result underscores the control DPN printing offers for patterning compounds ranging from small molecules and salts to organic macromolecules on a variety of substrates.

Example 5

Figure 14:
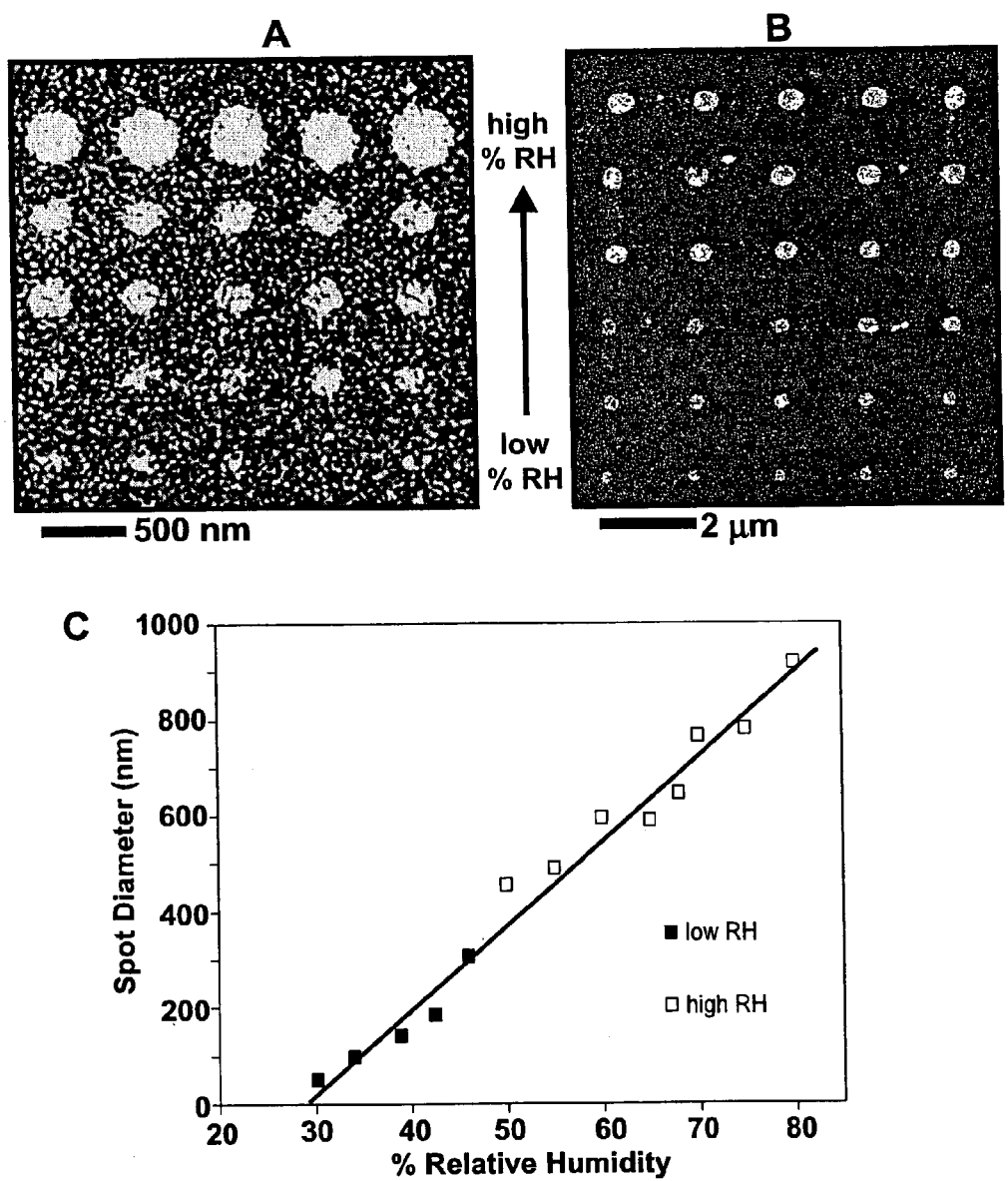
FIG. 14 illustrates the humidity dependence of DNA transport rate. Tapping mode AFM images of (A) DNA spots generated on polycrystalline Au with contact time of 10 s/spot, from 30-46% relative humidity (RH) (bottom to top); (B) 13 nm gold particles hybridized to DNA spots generated with contact time of 10 s/spot, from 50-80% relative humidity (bottom to top); (C) spot diameter vs. relative humidity for points in A and B.

On both gold and silicon oxide, the transport rate and pattern size of the DNA can be tailored with careful humidity control. It is thus possible to vary feature size over a large dynamic range on a reasonable time scale. For example, on gold, the diameter of a spot created by holding the AFM tip for 10 s changes from 50 to 300 nm with a relative humidity change of 15% (FIG. 13C; see also FIG. 14). This humidity dependence generally points to a mechanism for transport of DNA from an AFM tip to a surface, which is generally dependent on the water meniscus between the tip and substrate. See, for example, Piner et al., *Langmuir*, 15, 5457 (1999).

Example 6

Figure 15:
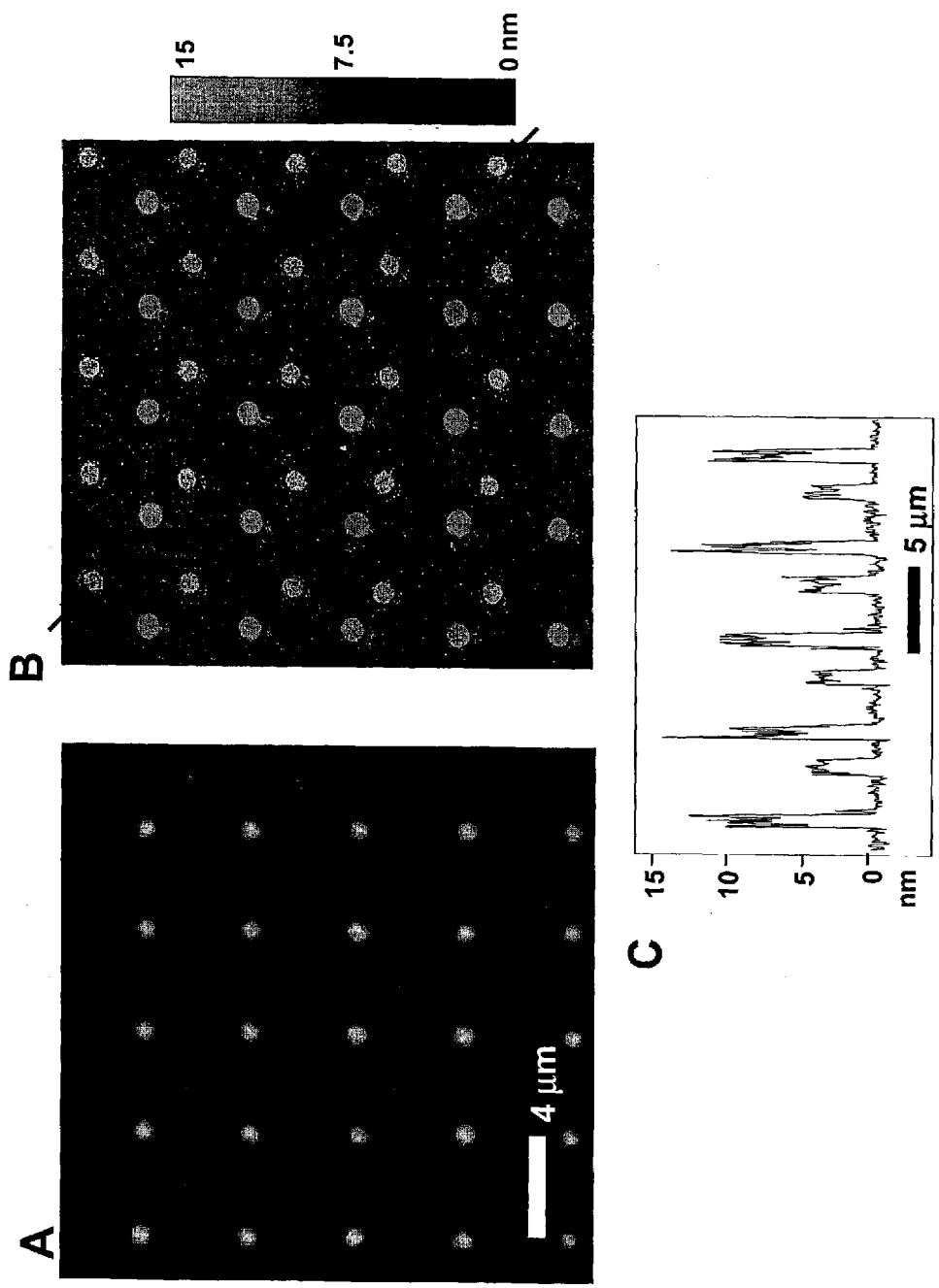
FIG. 15 illustrates direct patterning of multiple-DNA inks by DPN printing. (A) Combined red-green epifluorescence image of two different fluorophore-labeled sequences (Oregon Green 488-X and Texas Red-X) simulataneously hybridized to a two-sequence array deposited on an SiOx substrate by DPN printing. (B) Tapping mode AFM image of 5 (dark)- and 13 (light)-nm diameter gold nanoparticles assembled on the same pattern after dehybridization of the fluorophore-labeled DNA. The scale bar represents 4 microns. (C) The line plot was taken diagonally through both nanoparticle patterns, and the start and finish are indicated by the arrows in (B). The scale bar represents 4 microns.
Figure 16:
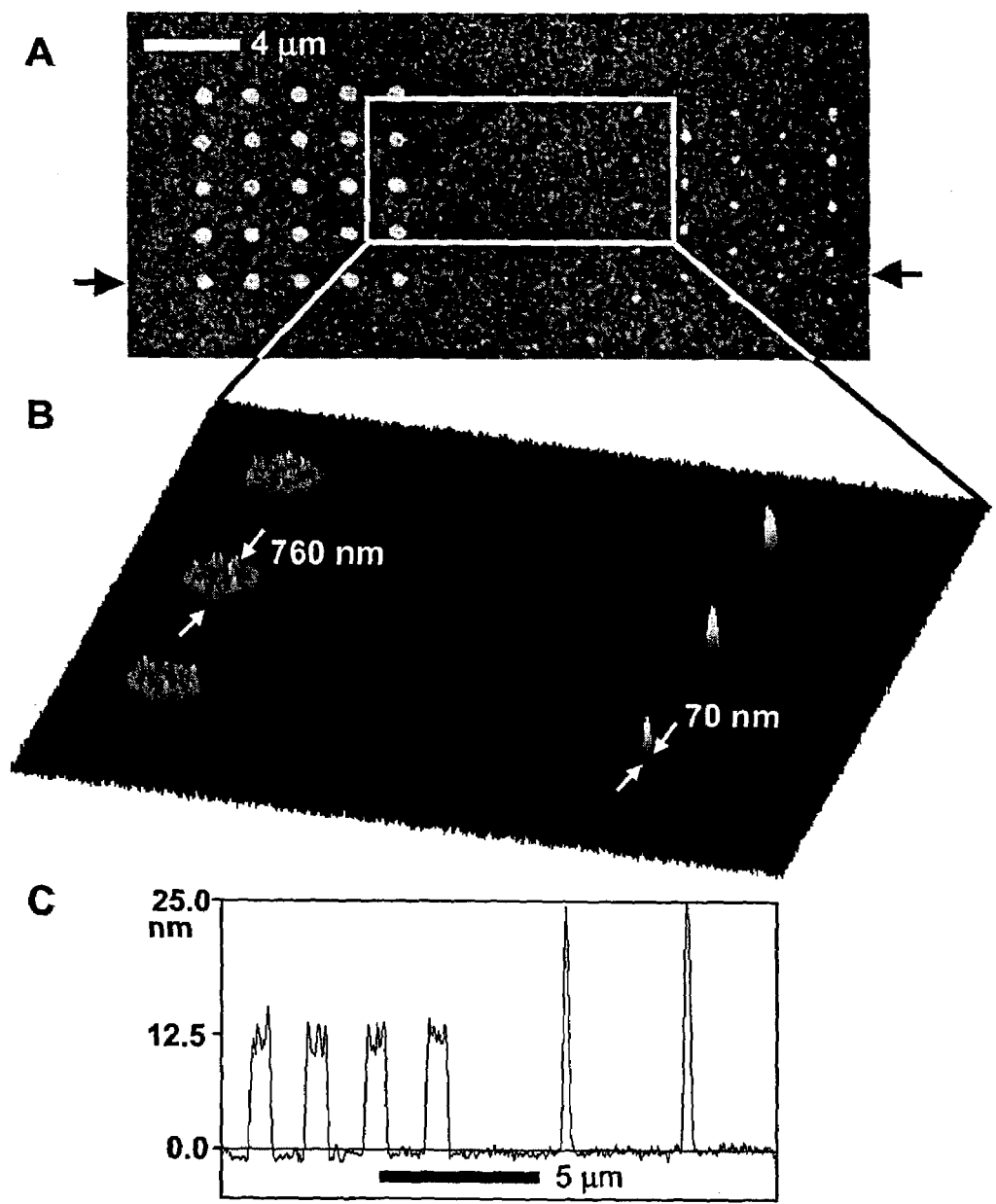
FIG. 16 illustrates AFM images of patterned gold substrates. (A) Tapping-mode AFM image of DNA patterns, C1 (square dot array) and C2 (triangular dot array) after ODT passivation. (B) Tapping-mode AFM image of 13 nm and 30 nm diameter gold nanoparticles hybridized selectively to C1 and C2 DNA patterns in the presence of L1 and L2 respectively. (C) Line scan showing height profile across patterns in A after hybridization to 13 and 30 nm diameter particles.

To demonstrate multi-DNA ink capabilities, DPN printing was used to prepare a two-component DNA array on an oxidized silicon substrate and verified its sequence-specific activity by hybridization with complementary fluorophore-labeled probes (FIGS. 15 and 16). To further verify the chemical integrity of the patterns, the same chip was treated with DI water to remove the fluorophore-labeled DNA and then exposed to a solution containing a mixture of 5- and 13-nm-diameter gold nanoparticles. The large and small particles were modified with DNA complementary to the first and second patterns, respectively. The particles selectively assembled on the correct patterns under appropriate hybridization conditions. This experiment not only shows how nanoparticles can be used as diagnostic probes in AFM-based screening procedures but also shows how nanostructures can be formed by the direct-write DPN approach to control and fabricate the assembly of nanoparticle-based architectures.

What is claimed is:

1. A method for generating nanoscale patterns of nucleic acid on a substrate comprising:
   modifying a scanning probe microscope tip to have a positive charge and form a modified tip;
   coating the modified tip with an ink composition comprising solvent, nucleic acid and inorganic salt;
   positioning the modified and coated scanning probe microscopic tip relative to a substrate so that the tip and substrate approach each other at a relative humidity sufficiently high so that nucleic acid is transferred from the tip to the substrate to form a stable nanoscale pattern on the substrate.

2. The method according to claim 1, wherein the tip is an atomic force microscope tip.

3. The method according to claim 1, wherein the tip is a hollow tip.

4. The method according to claim 1, wherein the tip is modified to have a positively charged amino group.

5. The method according to claim 1, wherein the relative humidity is at least about 25%.

6. The method according to claim 1, wherein the relative humidity is about 40% to about 100%.

7. The method according to claim 1, wherein the nucleic acid is a deoxyribose nucleic acid.

8. The method according to claim 1, wherein the nucleic acid is a single-stranded oligonucleotide.

9. The method according to claim 1, wherein the nucleic acid is modified to comprise a spacer group and a terminal group which provides for chemisorption or covalent bonding to the substrate.

10. The method according to claim 1, wherein the substrate is an electrical conductor.

11. The method according to claim 1, wherein the substrate is an electrical insulator.

12. The method according to claim 1, wherein the pattern has a lateral dimension of about 500 nm or less.

13. The method according to claim 1, wherein the pattern has a lateral dimension of about 200 nm or less.

14. The method according to claim 1, wherein the pattern has a lateral dimension of about 10 nm to about 100 nm.

15. The method according to claim 1, wherein the nucleic acid pattern can be hybridized with complementary nucleic acid.

16. The method according to claim 1, wherein the nucleic acid pattern can be hybridized with complementary nucleic acid, wherein the complementary nucleic acid is part of a probe.

17. The method according to claim 1, wherein the nucleic acid pattern can be hybridized with complementary nucleic acid, wherein the complementary nucleic acid is part of a linker which links the nucleic acid pattern to a probe.

18. The method according to claim 1, wherein the substrate is also passivated.

19. The method according to claim 1, wherein the tip is an atomic force microscope tip, the substrate is an electrical conductor, the nucleic acid is a deoxyribose nucleic acid, and the relative humidity is at least about 25%.

20. The method according to claim 1, wherein the tip is an atomic force microscope tip, the substrate is an electrical conductor, the nucleic acid is a deoxyribose nucleic acid, the relative humidity is at least about 25%, and the substrate is also passivated.

21. The method according to claim 1, wherein the tip is an atomic force microscope tip which is treated to contain a positive charge, the nucleic acid is a deoxyribose nucleic acid, and the relative humidity is about 25% to about 100%.

22. The method according to claim 1, wherein the tip is an atomic force microscope tip modified to be positively charged, the substrate is an electrical conductor or an electrical insulator, the nucleic acid is a deoxyribose nucleic acid which contains functional groups for covalent bonding or chemisorption to the substrate surface, the relative humidity is about 40% to about 50%, and the substrate is also passivated.

23. The method according to claim 1, wherein the tip is an atomic force microscope tip or a hollow tip, the substrate is an electrical conductor or an electrical insulator, the nucleic acid is a deoxyribose nucleic acid which contains functional groups for covalent bonding or chemisorption to the substrate surface, the relative humidity is at least about 25%, and the substrate is also passivated.

24. A nucleic acid nanoarray comprising a substrate and a plurality of patterns of nucleic acid on the substrate, wherein the patterns of nucleic acid are chemisorbed or covalently bonded to the substrate, have lateral dimensions of about 1,000 nm or less and are separated from each other by distances of 1,000 nm or less, and have a pattern density of at least 100,000 per square centimeter, and are hybridizable to complementary nucleic acids, and wherein the patterns of nucleic acid are formed by the method according to claim 1.

25. A method comprising:

modifying a scanning probe microscope tip to have amino functionality to form a modified tip;

coating the modified tip with an ink composition comprising nucleic acid;

positioning the modified and coated scanning probe microscopic tip relative to a substrate so that the tip and substrate approach each other at a relative humidity sufficiently high so that nucleic acid is transferred from the tip to the substrate to form a stable patterns on the substrate.

26. A method according to claim 25, wherein the scanning probe microscope tip is an atomic force microscope tip.

27. A method according to claim 25, wherein the modifying is carried out with an aminosilane compound.

* * * * *

```
                           SEQUENCE LISTING

<160> NUMBER OF SEQ ID NOS: 13

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucletoide

<400> SEQUENCE: 1
gagggattat tgtta                                                      15

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucletoide

<400> SEQUENCE: 2
agtcgcttct accat                                                      15

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucletoide

<400> SEQUENCE: 3
agagttgagc tataacaata atccctc                                         27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucletoide

<400> SEQUENCE: 4
agagttgagc taatggtaga agcgact                                         27

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucletoide
```

-continued

```
<400> SEQUENCE: 5
tagctcaact ctaaaaaaaa aaaaaaaaaa aa                                   32

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucletoide

<400> SEQUENCE: 6
atccttatca atatt                                                      15

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucletoide

<400> SEQUENCE: 7
cgcattcagg at                                                         12

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucletoide

<400> SEQUENCE: 8
ggattattgt taaatattga taaggat                                         27

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucletoide

<400> SEQUENCE: 9
tacgagttga gaatcctgaa tgcg                                            24

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucletoide

<400> SEQUENCE: 10
ggattattgt taaat                                                      15

<210> SEQ ID NO 11
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucletoide

<400> SEQUENCE: 11
```

```
                                     -continued tacgagttga ga                                                            12

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucletoide

<400> SEQUENCE: 12
tctcaactcg taaaaaaaaa aa                                                 22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucletoide

<400> SEQUENCE: 13
taacaataat ccaaaaaaaa aa                                                 22
```